(12) United States Patent
Mach et al.

(10) Patent No.: US 12,727,755 B2
(45) Date of Patent: Sep. 8, 2026

(54) SYSTEMS AND METHODS FOR MEDICAL IMAGING

(71) Applicant: ACTIV Surgical, Inc., Boston, MA (US)

(72) Inventors: Anderson Mach, Boston, MA (US); Stephen Tully, Boston, MA (US); Vasiliy Buharin, Boston, MA (US); Liam O'Shea, Boston, MA (US); Allen Bates, Boston, MA (US)

(73) Assignee: ACTIV Surgical, Inc., Boston, MA (US)

( * ) Notice: Subject to any disclaimer, the term of this patent is extended or adjusted under 35 U.S.C. 154(b) by 14 days.

(21) Appl. No.: 18/710,574

(22) PCT Filed: Nov. 16, 2022

(86) PCT No.: PCT/US2022/050147
§ 371 (c)(1),
(2) Date: May 15, 2024

(87) PCT Pub. No.: WO2023/091515
PCT Pub. Date: May 25, 2023

(65) Prior Publication Data

US 2025/0025039 A1 Jan. 23, 2025

Related U.S. Application Data

(60) Provisional application No. 63/280,029, filed on Nov. 16, 2021.

(51) Int. Cl.
*A61B 1/313* (2006.01)
*A61B 1/06* (2006.01)

(52) U.S. Cl.
CPC .......... *A61B 1/3132* (2013.01); *A61B 1/0638* (2013.01)

(58) Field of Classification Search
CPC .............. A61B 1/0005; A61B 1/00186; A61B 1/00193; A61B 1/00194; A61B 1/022;
(Continued)

(56) References Cited

U.S. PATENT DOCUMENTS 4,349,014 A 9/1982 Takamatsu
4,576,456 A 3/1986 Okino et al.
(Continued)

FOREIGN PATENT DOCUMENTS

CN 102770071 A 11/2012
CN 103169446 A 6/2013
(Continued)

OTHER PUBLICATIONS

PCT Notification of Transmittal of the International Search Report and the Written Opinion of the International Searching Authority, or the Declaration, International Searching Authority, International Application No. PCT/US2022/050147, mailed Apr. 6, 2023.
(Continued)

*Primary Examiner* — Michael J Carey
*Assistant Examiner* — Stephen Floyd London
(74) *Attorney, Agent, or Firm* — Cesari and McKenna, LLP

(57) ABSTRACT

The present disclosure provides systems and methods for medical imaging. An imaging device may comprise a housing, an insertion portion of housing, the insertion portion may have an elongated optical axis, where a first optical signal and a second optical signal may be transmitted along the elongated optical axis, where the first optical signal and the second optical signal may comprise a distinct wavelength range and a first imaging unit integrated within the housing, a beam splitter configured to deliver the first optical signal to the first imaging unit and configured to deliver the second optical signal to a second imaging unit. The imaging
(Continued)

device may comprise a coupling portion along an axis of the second optical signal configured to releasably couple the second imaging unit to the housing.

19 Claims, 21 Drawing Sheets

(58) Field of Classification Search
CPC ......... A61B 1/042; A61B 1/046; A61B 1/053; A61B 1/055; A61B 1/0638; A61B 2090/363
See application file for complete search history.

(56) References Cited

U.S. PATENT DOCUMENTS 4,592,632 A 6/1986 Renold
4,844,071 A 7/1989 Chen et al.
4,905,082 A 2/1990 Nishigaki et al.
4,974,076 A 11/1990 Nakamura et al.
5,748,930 A 5/1998 Prakash
5,749,830 A 5/1998 Kaneko et al.
5,980,450 A 11/1999 Thompson
6,069,698 A 5/2000 Ozawa et al.
6,088,105 A 7/2000 Link
6,346,073 B1 2/2002 Thompson
6,373,963 B1 4/2002 Demers et al.
6,438,302 B1 8/2002 Utsui et al.
6,491,702 B2 12/2002 Heilbrun et al.
6,503,195 B1 1/2003 Keller et al.
6,537,211 B1 3/2003 Wang et al.
6,542,249 B1 4/2003 Kofman et al.
6,549,288 B1 4/2003 Migdal et al.
6,563,105 B2 5/2003 Seibel et al.
6,564,086 B2 5/2003 Marchitto et al.
6,613,041 B1 9/2003 Schrunder
6,635,011 B1 10/2003 Ozawa et al.
6,697,164 B1 2/2004 Babayoff et al.
6,800,057 B2 10/2004 Tsujita et al.
6,850,872 B1 2/2005 Marschner et al.
6,873,867 B2 3/2005 Vilsmeier
6,885,464 B1 4/2005 Pfeiffer et al.
RE38,800 E 9/2005 Barbour
6,965,690 B2 11/2005 Matsumoto
6,977,732 B2 12/2005 Chen et al.
6,987,531 B2 1/2006 Kamon
7,006,236 B2 2/2006 Tomasi et al.
7,068,825 B2 6/2006 Rubbert et al.
7,092,107 B2 8/2006 Babayoff et al.
7,099,732 B2 8/2006 Geng
7,124,066 B2 10/2006 Marschner
7,152,024 B2 12/2006 Marschner
7,184,150 B2 2/2007 Quadling
7,200,262 B2 4/2007 Sawada
7,224,384 B1 5/2007 Iddan
7,230,725 B2 6/2007 Babayoff
7,242,997 B2 7/2007 Geng
7,305,110 B2 12/2007 Rubbert
7,313,264 B2 12/2007 Crampton
7,319,529 B2 1/2008 Babayoff
7,363,201 B2 4/2008 Marschner
7,385,708 B2 6/2008 Ackerman
7,433,807 B2 10/2008 Marschner
7,435,217 B2 10/2008 Wiklof
7,450,783 B2 11/2008 Talapov
7,477,402 B2 1/2009 Babayoff
7,489,408 B2 2/2009 Harding
7,491,956 B2 2/2009 Knoche
7,492,927 B2 2/2009 Marschner
7,511,829 B2 3/2009 Babayoff
7,522,764 B2 4/2009 Schwotzer
7,577,299 B2 8/2009 Kawamata
7,620,209 B2 11/2009 Stevick
7,630,089 B2 12/2009 Babayoff
7,704,206 B2 4/2010 Suzuki
7,724,378 B2 5/2010 Babayoff
7,724,932 B2 5/2010 Ernst
7,751,871 B2 7/2010 Rubbert
7,763,841 B1 7/2010 McEldowney
7,794,388 B2 9/2010 Draxinger
7,821,649 B2 10/2010 Bendall
7,854,700 B2 12/2010 Orihara
7,898,651 B2 3/2011 Hu et al.
7,944,569 B2 5/2011 Babayoff
7,951,073 B2 5/2011 Freed
7,961,912 B2 6/2011 Stevick et al.
7,967,743 B2 6/2011 Ishihara
7,990,548 B2 8/2011 Babayoff et al.
7,995,798 B2 8/2011 Krupnik et al.
8,027,710 B1 9/2011 Dannan
8,038,609 B2 10/2011 Kohno et al.
8,084,753 B2 12/2011 Joshi et al.
8,194,122 B2 6/2012 Amling et al.
8,264,536 B2 9/2012 McEldowney
8,279,418 B2 10/2012 Yee et al.
8,280,152 B2 10/2012 Thiel et al.
8,310,683 B2 11/2012 Babayoff et al.
8,320,621 B2 11/2012 McEldowney
8,326,020 B2 12/2012 Lee et al.
8,330,804 B2 12/2012 Lutian et al.
8,400,494 B2 3/2013 Zalevsky et al.
8,406,859 B2 3/2013 Zuzak et al.
8,471,897 B2 6/2013 Rodriguez Ramos
8,517,928 B2 8/2013 Orihara
8,553,939 B2 10/2013 Craig et al.
8,558,873 B2 10/2013 McEldowney
8,593,507 B2 11/2013 Yahav
8,610,665 B2 12/2013 Craig et al.
8,649,024 B2 2/2014 Colonna De Lega
8,659,765 B2 2/2014 Ando
8,723,118 B2 5/2014 McEldowney et al.
8,723,923 B2 5/2014 Bloom et al.
8,755,053 B2 6/2014 Fright et al.
8,792,098 B2 7/2014 Dewald et al.
8,803,952 B2 8/2014 Katz et al.
8,823,790 B2 9/2014 Dunn et al.
8,891,087 B2 11/2014 Zuzak et al.
8,896,594 B2 11/2014 Xiong et al.
8,974,378 B2 3/2015 Imaizumi et al.
9,001,190 B2 4/2015 Olivier, III et al.
9,057,784 B2 6/2015 Hudman
9,068,824 B2 6/2015 Findeisen et al.
9,070,194 B2 6/2015 Lee et al.
9,072,445 B2 7/2015 Berguer et al.
9,074,868 B2 7/2015 Bendall et al.
9,089,277 B2 7/2015 Babayoff et al.
9,119,552 B2 9/2015 Baumann et al.
9,135,502 B2 9/2015 Haker et al.
9,142,025 B2 9/2015 Park et al.
9,147,253 B2 9/2015 Yee et al.
9,149,348 B2 10/2015 Wu et al.
9,155,480 B2 10/2015 Thakor et al.
9,157,728 B2 10/2015 Ogawa
9,157,733 B2 10/2015 Dillon et al.
9,198,578 B2 12/2015 Zuzak et al.
9,204,952 B2 12/2015 Lampalzer
9,220,570 B2 12/2015 Kim et al.
9,226,645 B2 1/2016 Ntziachristos
9,226,673 B2 1/2016 Ferguson, Jr
9,247,865 B2 2/2016 Igarashi et al.
9,254,076 B2 2/2016 McDowall
9,254,078 B2 2/2016 McDowall
9,254,103 B2 2/2016 Krishnaswamy
9,261,356 B2 2/2016 Lampert et al.
9,261,358 B2 2/2016 Atiya et al.
9,271,633 B2 3/2016 Scott et al.
9,271,658 B2 3/2016 Ferguson, Jr.
9,274,047 B2 3/2016 Velten et al.
9,282,926 B2 3/2016 Schwotzer et al.
9,294,758 B2 3/2016 Xiong et al.
9,297,889 B2 3/2016 Hudman et al.
9,304,603 B2 4/2016 Miller
9,330,464 B1 5/2016 Ackerman et al.
9,345,389 B2 5/2016 Nie et al.

(56) References Cited

U.S. PATENT DOCUMENTS 9,345,392 B2 5/2016 Saito
9,345,397 B2 5/2016 Taylor et al.
9,351,643 B2 5/2016 Sharonov
9,364,300 B2 6/2016 Tchouprakov et al.
9,375,844 B2 6/2016 Itkowitz et al.
9,377,295 B2 6/2016 Fright et al.
9,380,224 B2 6/2016 Keskin et al.
9,389,068 B2 7/2016 Ri
9,404,741 B2 8/2016 Schick
9,432,593 B2 8/2016 Yang et al.
9,439,568 B2 9/2016 Atiya et al.
9,443,310 B2 9/2016 Hudman et al.
9,444,981 B2 9/2016 Bellis et al.
9,451,872 B2 9/2016 Yokota
9,462,253 B2 10/2016 Hudman et al.
9,471,864 B2 10/2016 Zatloukal et al.
9,491,441 B2 11/2016 Sarmast et al.
9,494,418 B2 11/2016 Schmidt
9,506,749 B2 11/2016 Bellis et al.
9,513,113 B2 12/2016 Yang et al.
9,513,768 B2 12/2016 Zhao et al.
9,545,220 B2 1/2017 Sidlesky
9,554,692 B2 1/2017 Levy
9,557,574 B2 1/2017 McEldowney
9,581,802 B2 2/2017 Yokota
9,615,901 B2 4/2017 Babayoff et al.
9,622,644 B2 4/2017 Yokota
9,622,662 B2 4/2017 Zuzak et al.
9,638,801 B2 5/2017 Boufounos et al.
9,674,436 B2 6/2017 Crane et al.
9,675,429 B2 6/2017 Lampert et al.
9,690,984 B2 6/2017 Butler et al.
9,696,427 B2 7/2017 Wilson et al.
9,720,506 B2 8/2017 Kim et al.
9,729,860 B2 8/2017 Cohen et al.
9,737,239 B2 8/2017 Kimmel
9,739,594 B2 8/2017 Koerner et al.
9,746,318 B2 8/2017 Sugano
9,752,867 B2 9/2017 Atiya et al.
9,782,056 B2 10/2017 McDowall
9,788,903 B2 10/2017 Kim et al.
9,799,117 B2 10/2017 Chen et al.
9,817,159 B2 11/2017 Hudman
9,833,145 B2 12/2017 Jeong et al.
9,841,496 B2 12/2017 Hudman
9,844,427 B2 12/2017 Atiya et al.
9,901,409 B2 2/2018 Yang et al.
9,918,640 B2 3/2018 Ntziachristos et al.
9,922,249 B2 3/2018 Kang et al.
9,939,258 B2 4/2018 Lampert et al.
9,943,271 B2 4/2018 Dirauf et al.
9,947,099 B2 4/2018 Bleyer et al.
9,953,428 B2 4/2018 Gren et al.
9,955,140 B2 4/2018 Rhemann et al.
9,955,861 B2 5/2018 Gao et al.
9,958,585 B2 5/2018 Powell et al.
9,958,758 B2 5/2018 Hudman
9,962,244 B2 5/2018 Esbech et al.
9,970,753 B2 5/2018 Han et al.
10,011,014 B2 7/2018 Divoky et al.
10,018,464 B2 7/2018 Boles et al.
10,024,968 B2 7/2018 Hudman et al.
10,039,439 B2 8/2018 Aoyama
10,045,882 B2 8/2018 Balicki et al.
10,055,856 B2 8/2018 Sabater et al.
10,058,256 B2 8/2018 Chen et al.
10,066,997 B2 9/2018 Korner et al.
10,089,737 B2 10/2018 Krieger et al.
10,169,862 B2 1/2019 Andre et al.
10,244,991 B2 4/2019 Shademan et al.
10,390,718 B2 8/2019 Chen et al.
10,398,519 B2 9/2019 Kim et al.
10,575,737 B2 3/2020 Andre et al.
10,675,040 B2 6/2020 Kim et al.
10,681,259 B2 6/2020 Ichiki et al.
10,694,117 B2 6/2020 Frangioni
10,722,173 B2 7/2020 Chen et al.
10,792,492 B2 10/2020 Chen et al.
10,925,465 B2 2/2021 Tully et al.
10,948,350 B2 3/2021 Ferguson, Jr. et al.
10,966,597 B2 4/2021 Yamazoe et al.
11,135,028 B2 10/2021 Kim et al.
11,278,220 B2 3/2022 Tucker et al.
11,389,051 B2 7/2022 Tully et al.
11,754,828 B2 9/2023 Tully et al.
11,977,218 B2 5/2024 Dehghani et al.
12,416,798 B2 9/2025 Dehghani et al.
2001/0030983 A1 10/2001 Yuri et al.
2002/0021355 A1 2/2002 Utsui et al.
2002/0022768 A1 2/2002 Utsui
2002/0087047 A1 7/2002 Remijan
2003/0050532 A1 3/2003 Doguchi
2003/0176768 A1 9/2003 Gono
2003/0195623 A1 10/2003 Marchitto et al.
2004/0257438 A1 12/2004 Doguchi
2005/0010084 A1 1/2005 Tsai
2005/0096515 A1 5/2005 Geng
2005/0220447 A1 10/2005 Ito
2005/0267329 A1 12/2005 Konstorum et al.
2006/0173240 A1 8/2006 Fukuyama
2007/0055103 A1 3/2007 Hoefig et al.
2007/0115484 A1 5/2007 Huang et al.
2007/0146719 A1 6/2007 Wedel
2007/0165243 A1 7/2007 Kang et al.
2007/0276185 A1 11/2007 Gono
2007/0280423 A1 12/2007 Schmidt
2008/0107305 A1 5/2008 Vanderkooy et al.
2008/0218826 A1 9/2008 DeSaulniers
2008/0266391 A1 10/2008 Lee et al.
2009/0216085 A1 8/2009 Yamazaki
2009/0221874 A1 9/2009 Vinther et al.
2009/0244260 A1 10/2009 Takahashi et al.
2009/0289200 A1 11/2009 Ishii
2010/0097454 A1 4/2010 Kubo
2010/0113921 A1 5/2010 Fear et al.
2010/0210904 A1 8/2010 Cline et al.
2011/0015518 A1 1/2011 Schmidt et al.
2011/0043609 A1 2/2011 Choi et al.
2011/0057930 A1 3/2011 Keller et al.
2011/0069162 A1 3/2011 Ozawa et al.
2011/0071352 A1 3/2011 Ozawa et al.
2011/0080471 A1 4/2011 Song et al.
2011/0123098 A1 5/2011 Ernst
2011/0221879 A1 9/2011 Schmidt
2011/0245844 A1 10/2011 Jinno
2012/0075432 A1 3/2012 Bilbrey et al.
2012/0095354 A1 4/2012 Dunn et al.
2012/0101348 A1 4/2012 Yamaguchi et al.
2012/0165681 A1 6/2012 Keller
2012/0206587 A1 8/2012 Oz et al.
2012/0307512 A1 12/2012 Cogger et al.
2012/0310098 A1 12/2012 Popovic
2013/0023732 A1 1/2013 Kim et al.
2013/0041267 A1 2/2013 Ntziachristos et al.
2013/0253313 A1 9/2013 Kang et al.
2013/0274596 A1 10/2013 Azizian et al.
2013/0296712 A1 11/2013 Durvasula
2014/0031665 A1 1/2014 Pinto
2014/0051923 A1 2/2014 Mirza et al.
2014/0052005 A1 2/2014 Yokota
2014/0071257 A1 3/2014 Yokota
2014/0092281 A1 4/2014 Nisenzon et al.
2014/0194747 A1 7/2014 Kruglick et al.
2014/0221749 A1 8/2014 Grant et al.
2014/0309495 A1 10/2014 Kirma et al.
2014/0378845 A1 12/2014 Nadkarni
2015/0099925 A1 4/2015 Davidson et al.
2015/0164329 A1 6/2015 Schmidt et al.
2015/0238276 A1 8/2015 Atarot et al.
2015/0377613 A1 12/2015 Small et al.
2015/0381909 A1 12/2015 Butte et al.
2016/0022126 A1* 1/2016 Ramesh .............. A61B 1/0638 600/109
2016/0100908 A1 4/2016 Tesar

(56) References Cited

U.S. PATENT DOCUMENTS

2016/0128553 A1 5/2016 Geng
2016/0139039 A1 5/2016 Ikehara et al.
2016/0239978 A1 8/2016 Cole et al.
2016/0260206 A1 9/2016 Jung et al.
2016/0262615 A1 9/2016 Jung et al.
2016/0278678 A1 9/2016 Valdes et al.
2016/0300348 A1 10/2016 Nadeau et al.
2016/0302880 A1 10/2016 Uhlemann et al.
2016/0307325 A1 10/2016 Wang
2016/0307326 A1 10/2016 Wang
2016/0309068 A1 10/2016 Nadeau et al.
2016/0335472 A1 11/2016 Lee et al.
2017/0014030 A1 1/2017 Rentschler
2017/0020393 A1 1/2017 Rentschler
2017/0026633 A1 1/2017 Riza
2017/0030710 A1 2/2017 Rentschler
2017/0032531 A1 2/2017 Nagata
2017/0059305 A1 3/2017 Nonn et al.
2017/0059849 A1 3/2017 Daidoji et al.
2017/0079724 A1 3/2017 Yang et al.
2017/0095299 A1 4/2017 Hendrick et al.
2017/0100024 A1 4/2017 Shahmoon et al.
2017/0143237 A1 5/2017 Yokota
2017/0155818 A1 6/2017 Bonnet
2017/0164836 A1 6/2017 Krishnaswamy
2017/0172382 A1 6/2017 Nir et al.
2017/0172384 A1 6/2017 Yokota
2017/0172394 A1 6/2017 Scott et al.
2017/0209031 A1 7/2017 Nakamura
2017/0224274 A1 8/2017 Chen et al.
2017/0227942 A1 8/2017 Thomson et al.
2017/0228879 A1 8/2017 Sato
2017/0251900 A1 9/2017 Hansen
2017/0280970 A1 10/2017 Sartor et al.
2017/0311778 A1 11/2017 Hasser
2017/0328704 A1 11/2017 Atiya et al.
2017/0347043 A1 11/2017 Rephaeli et al.
2017/0351103 A1 12/2017 Duckett et al.
2017/0366773 A1 12/2017 Kiraly et al.
2018/0003943 A1 1/2018 Chan
2018/0008371 A1 1/2018 Manus
2018/0042466 A1 2/2018 Kang et al.
2018/0047165 A1 2/2018 Sato
2018/0104009 A1 4/2018 Abhari et al.
2018/0116520 A1* 5/2018 Yamamoto ........... A61B 1/0002
2018/0125586 A1 5/2018 Sela et al.
2018/0165823 A1 6/2018 Ludwig
2018/0174318 A1 6/2018 Wang et al.
2018/0235715 A1 8/2018 Amiot et al.
2018/0243043 A1 8/2018 Michihata et al.
2018/0279954 A1 10/2018 Hayam
2018/0360299 A1 12/2018 Kishima
2019/0000308 A1 1/2019 Duckett, III
2019/0159663 A1* 5/2019 Krstajic ............... A61B 5/0071
2019/0200848 A1* 7/2019 McDowall ............. A61B 34/35
2019/0239730 A1 8/2019 Myung et al.
2019/0246873 A1 8/2019 Lu
2019/0265490 A1 8/2019 Duckett
2019/0335104 A1* 10/2019 Sugie ................. A61B 1/00096
2020/0107710 A1 4/2020 Duckett et al.
2020/0143545 A1 5/2020 Weng et al.
2020/0192017 A1 6/2020 Dulk
2020/0246105 A1 8/2020 Levesque et al.
2020/0305721 A1 10/2020 Chen et al.
2020/0315432 A1* 10/2020 Tully ..................... H04N 23/55
2020/0405152 A1* 12/2020 Hirano ............... G02B 23/2453
2021/0030277 A1 2/2021 Ferguson, Jr.
2021/0144345 A1* 5/2021 Takashima ............ G01J 3/0205
2021/0282630 A1 9/2021 Kikuchi et al.
2021/0282654 A1 9/2021 Cha et al.
2021/0338060 A1 11/2021 Tully et al.
2022/0021807 A1* 1/2022 Weise .................... A61B 1/042
2022/0115882 A1 4/2022 Clark
2022/0287553 A1 9/2022 Tully et al.
2022/0377217 A1 11/2022 Dehghani et al.
2022/0378280 A1 12/2022 Tully et al.
2023/0105882 A1 4/2023 Abe
2023/0125959 A1* 4/2023 Joshi .................. A61B 1/00009 600/160
2024/0353669 A1 10/2024 Dehghani et al.

FOREIGN PATENT DOCUMENTS

CN 107124547 A 9/2017
CN 107510430 A 12/2017
EP 1489406 A1 12/2004
EP 2625998 A 8/2013
EP 2604177 B1 4/2016
JP H10290780 A 11/1998
JP 2006187427 A 7/2006
JP 2007037783 A 2/2007
JP 2007229135 A 9/2007
JP 2009022652 A 2/2009
JP 2009095554 A 5/2009
JP 2010017377 A 1/2010
JP 2015231498 A 12/2015
JP 2018042676 A 3/2025
KR 20170051264 A 5/2017
KR 20180066645 A 6/2018
WO WO-201009644 7 A2 8/2010
WO WO-2010096453 A1 8/2010
WO WO-2012096878 A2 7/2012
WO WO-2014152753 A1 9/2014
WO WO-2016061052 A1 4/2016
WO WO-20161537 41 A1 9/2016
WO WO-2017075602 A1 5/2017
WO 2018021035 A1 2/2018
WO WO-2019045971 A1 3/2019
WO WO-2020006454 A1 1/2020
WO WO-2020210168 10/2020
WO WO-2021035094 2/2021
WO WO-2021035094 A1 2/2021
WO 2021108450 A1 6/2021
WO WO-2022029308 A1 2/2022
WO WO-2022058499 A1 3/2022
WO WO-2023091515 A1 5/2023
WO WO-2023205456 A1 10/2023

OTHER PUBLICATIONS

Korean Office Action dated Aug. 13, 2025, Korean Patent Application No. 10-2021-7036131, 8 pages with translation.

Bray et al. Endoscopic laser speckle imaging of tissue blood flow: applications in the human knee. Journal of Orthopaedic Research, pp. 1650-1659 (2006).

Cha et al. Dual-display laparascopic laser speckle contrast imaging for real-time surgical assistance. Biomedical Optics Express, 9(12) pp. 1-20 (2018). Available at https://hsrc.himmelfarb.gwu.edu/cgi/viewcontent.cgi?article=3662&context=smhs_peds_facpubs.

Dunn, et al. Laser speckle contrast imaging in biomedical optics. Journal of Biomedical Optics 15(1), 011109 (Jan./Feb. 2010).

EP20788162.4 Extended European Search Report dated Mar. 7, 2023.

EP20855369.3 Supplementary European Search Report dated Aug. 10, 2023,.

EP application No. 23792607.6—Supplemental European Search Report, mailed Jul. 22, 2025, 12 pages.

Holstein-Rathlou et al. Nephron blood flow dynamics measured by laser speckle contrast imaging. Am J Phsiol Renal Physiol 300: F319-F329, 2011.

Kadambi et al. Rethinking machine vision time of flight with GHz heterodying. IEEE Access. vol. 5, 1-13, Nov. 2017.

Li et al. SH-ToF: Micro Resolution Time-of-Flight Imaging with Superheterodyne Interferometry, IEEE ICCP, 2018: 1-10.

PCT/US2020/047275 International Search Report & Written Opinion dated Feb. 1, 2021.

PCT/US20/26920 Search Report and Written Opinion dated Jun. 26, 2020.

PCT/US2023/019457 International Search Report and Written Opinion dated Aug. 21, 2023.

(56) References Cited

OTHER PUBLICATIONS

Richards et al. Intraoperative laser speckle contrast imaging with retrospective motion correction for quantitative assessment of cerebral blood flow. Neurophotonics 1(1), 015006 (Jul.-Sep. 2014).
Richards et al. Low-cost laser speckle contrast imaging of blood flow using a webcam. 2013 Optical Society of America.
U.S. Appl. No. 17/150,708 Notice of Allowance dated Apr. 12, 2022.
U.S. Appl. No. 16/882,297 Notice of Allowance dated Nov. 6, 2020.
U.S. Appl. No. 16/882,297 Office Action dated Aug. 7, 2020.
U.S. Appl. No. 17/150,708 Office Action dated Oct. 26, 2021.
U.S. Appl. No. 17/838,469 Office Action dated Jun. 9, 2023.
U.S. Appl. No. 18/365,839, Co-pending, inventors Tully; Stephen et al., filed Aug. 4, 2023.
U.S. Appl. No. 17/838,469 Notice of Allowance dated Jul. 20, 2023.
EP23792607.6 Extended European Search Report dated Jul. 22, 2025.
Boas, et al. Laser speckle contrast imaging in biomedical optics. J Biomed Opt. Jan.-Feb. 2010;15(1):011109. doi: 10.1117/1.3285504. 12 pages.
U.S. Appl. No. 18/604,327, inventors Tully; Stephen et al., filed Mar. 13, 2024.
U.S. Appl. No. 18/614,393, inventors Dehghani; Hossein et al., filed Mar. 22, 2024.
U.S. Appl. No. 18/630,502, inventors Tully; Stephen et al., filed Apr. 9, 2024.
EP20855369.3 Extended European Search Report dated Nov. 14, 2023.
EP20892307.8 Extended European Search Report dated Nov. 6, 2023.
PCT/US2020/026920 International Preliminary Report on Patentability dated Sep. 28, 2021.
PCT/US2020/062086 International Search Report and Written Opinion dated Feb. 10, 2021.
U.S. Appl. No. 17/673,324 Notice of Allowance dated Dec. 26, 2023.
U.S. Appl. No. 17/673,324 Office Action dated Sep. 8, 2023.
U.S. Appl. No. 17/752,617 Office Action dated Jul. 13, 2023.
U.S. Appl. No. 17/752,617 Office Action dated Mar. 6, 2023.
U.S. Appl. No. 17/752,617 Office Action dated Oct. 12, 2023.
U.S. Appl. No. 18/614,393 Office Action dated Jan. 3, 2025.
Supplemental European Search Report, European Application No. EP 2289 6442, dated Dec. 1, 2025, 11 pages.

* cited by examiner 100
102
103
104
106
110
101
114
109
108
120
122

105
102
110
107
120
122
150

SYSTEMS AND METHODS FOR MEDICAL IMAGING

CROSS-REFERENCE

This application is the National Stage of International Application No. PCT/US2022/050147, filed Nov. 16, 2022, which claims the benefit of U.S. Provisional Application No. 63/280,029, filed on Nov. 16, 2021. The contents of both applications are hereby incorporated by reference in their entirety.

BACKGROUND

Medical imaging technology such as scopes may be used to capture images or video data of internal anatomical or physiological features of a subject or patient during medical or surgical procedures. The images or video data captured may be processed and manipulated to provide medical practitioners with a visualization of internal structures or processes within a patient or subject.

SUMMARY

Images or video data of internal anatomical or physiological features may be obtained using a scope (e.g., an endoscope). However, the images or video data obtained may be limited to only the visible spectrum and can often fail to provide visual details on complex anatomy or critical structures beneath the tissue surface. In some cases, the images or video data may not show invisible features of the target site in real-time, e.g., blood perfusion, cardiac output, hepatic function, etc. As a result, incomplete or incorrect analysis of the target site may lead to unintended tissue damage during surgical procedures.

Some commercially available imaging systems may be used to obtain images or video data of internal anatomical or physiological features. However, these imaging systems may have large footprints that take up valuable space within a cramped operating room, which can make the imaging systems unwieldy and difficult to maneuver or operate.

In some instances, the imaging systems may comprise a scope assembly which includes a scope, such as an endoscope, attached to an imaging device or module. Scopes used in operating rooms may have different sizes, shapes, and/or performance characteristics—all which may require calibration to use in a scope-based imaging system. In some cases, the optical properties or parameters of an imaging system may need to be calibrated each time a new component (e.g., an imaging device or module, or a scope) is used or substituted for another component. In some cases, the imaging system may require the combination of an attached imaging module (e.g., with an infrared sensor) with an attached imaging unit (with visible light sensor), which may result in a larger footprint and increased weight when combined together.

The present disclosure addresses at least above of the abovementioned shortcomings.

In an aspect, the present disclosure provides an imaging device. The imaging device may comprise: a housing; an insertion portion of housing, the insertion portion having an elongated optical axis, wherein a first optical signal and a second optical signal are transmitted along the elongated optical axis, wherein the first optical signal and the second optical signal each comprise a distinct wavelength range; a first imaging unit integrated within the housing; a beam splitter configured to deliver the first optical signal to the first imaging unit and configured to deliver the second optical signal to a second imaging unit; and a coupling portion along an axis of the second optical signal, wherein the coupling portion is configured to releasably couple the second imaging unit to the housing.

In some embodiments, the housing comprising the first imaging unit is hermetically sealed. In some embodiments, the first imaging unit, the second imaging unit, or both comprises an imaging sensor. In some embodiments, the imaging sensor comprises an infrared sensor. In some embodiments, the first imaging unit, the second imaging unit, or both comprises a camera or a sensor for RGB imaging. In some embodiments, the first optical signal has a first range of wavelengths and the second optical signal has a second range of wavelengths. In some embodiments, the first range of wavelengths is greater than a threshold wavelength and the second range of wavelengths is less than the threshold wavelength. In some embodiments, the threshold wavelength is between about 700 nanometers (nm) to about 800 nm.

In some embodiments, the first optical signal is a laser speckle imaging signal, and wherein the second optical signal is an RGB imaging signal. In some embodiments, the first optical signal is an RGB imaging signal, and the second optical signal is a laser speckle imaging signal. In some embodiments, the first imaging unit and the second imaging unit have different imaging modalities. In some embodiments, the different imaging modalities comprise at least one imaging modality selected from the group consisting of an infrared imaging sensor for laser speckle imaging, a fluorescence imaging sensor for fluorescence imaging, a mosaic sensor for hyperspectral imaging, a short wave infrared (SWIR) sensor for SWIR imaging, and a depth sensor for depth imaging.

In some embodiments, the imaging device further comprises an image processor operatively coupled to the first imaging unit, the second imaging unit, or both, wherein the image processor is configured to process one or more images obtained using the first imaging unit, the second imaging unit, or both. In some embodiments, the one or more images comprise one or more images of a surgical scene, and wherein the image processor is configured to produce a visualization of a surgical scene. In some embodiments, the visualization of the surgical scene comprises a dynamic overlay of images. In some embodiments, the dynamic overlay of images comprises one or more imaging modalities, the one or more imaging modalities selected from the group consisting of: a laser speckle image, a depth image, a fluorescence image, and an RGB image of the surgical scene. In some embodiments, the dynamic overlay of images is adjustable based on a user input or selection of a desired imaging modality.

In some embodiments, the imaging device comprises a portion of a laparoscope or an endoscope. In some embodiments, a field of view of an image from the first imaging unit, the second imaging unit, or both comprises a marker configured to aid in positioning or alignment the first imaging unit relative to the second imaging unit. In some embodiments, the marker comprises a notch. In some embodiments, the marker comprises a fiducial marker. In some embodiments, the elongated optical path comprises one or more obstructions between one or more pairs of lenses, and wherein the one or more obstructions appear in the field of view as the marker. In some embodiments, the imaging device further comprises: an optical source configured to project one or more visual references onto the surgical scene, and wherein the one or more visual references appear in the field of view as the marker. In some embodiments, the elongated optical path comprises one or more lenses for adjusting a field of view or an angle of view of the surgical scene. In some embodiments, the elongated optical path comprises one or more rod lenses or objective assemblies. In some embodiments, the imaging module comprises one or more buttons for receiving a physical input from a user. In some embodiments, the physical input controls an operation of the first imaging unit; the second imaging unit; a processor coupled to the first imaging unit, the second imaging unit, or both; or any combination thereof.

In some embodiments, the elongated portion of the housing is rotatable relative to the first imaging unit. In some embodiments, the coupling portion comprises an eyepiece. In some embodiments, the elongated portion of the housing comprises one or more optical filters. In some embodiments, the one or more optical filters comprises a notch filter comprising an absorption band at an excitation wavelength for fluorescence imaging. In some embodiments, the beam splitter is a dichroic beam splitter. In some embodiments, the imaging device does not comprise a window or an eyepiece between the elongated portion of the housing and the beam splitter. In some embodiments, a focus of the first optical signal on the first imaging unit is fixed during manufacturing. In some embodiments, a focus of the first optical signal on the first imaging unit is substantially not adjustable by a user.

In another aspect, the present disclosure provides a system comprising the imaging device of any aspect or embodiment and the second imaging unit, wherein the second imaging unit is releasably attached to the imaging device. In some embodiments, the first imaging unit is rotatable relative to the second imaging unit, the elongated portion of the housing, or both.

In another aspect, the preset disclosure provides an imaging device, the imaging device may comprise: a housing; an insertion portion of housing, the insertion portion of the housing having an elongated optical axis, wherein a first optical signal and a second optical signal are transmitted along the elongated optical axis, wherein the first optical signal and the second optical signal each comprise a distinct wavelength range, wherein the insertion portion comprises an even number of pairs of lenses and an unpaired lens; a beam splitter positioned distal to the insertion portion configured to deliver the first optical signal to a first imaging unit and configured to deliver the second optical signal to a second imaging unit; a lens along a first imaging axis distal to the beam splitter, wherein an image distal to the lens on the first imaging portion is inverted; and a pair of lenses and an unpaired lens on a second imaging axis distal to the beam splitter, wherein an image distal to the unpaired lens on the second imaging axis is right-side-up.

In some embodiments, the housing comprising the first imaging unit is hermetically sealed. In some embodiments, the first imaging unit, the second imaging unit, or both comprises an imaging sensor. In some embodiments, the imaging sensor comprises an infrared sensor. In some embodiments, the first imaging unit, the second imaging unit, or both comprises a camera or a sensor for RGB imaging. The first optical signal has a first range of wavelengths and the second optical signal has a second range of wavelengths. In some embodiments, the first range of wavelengths is greater than a threshold wavelength and the second range of wavelengths is less than the threshold wavelength. In some embodiments, the threshold wavelength is between about 700 nanometers (nm) to about 800 nm. In some embodiments, the first optical signal a laser speckle imaging signal, and wherein the second optical signal an RGB imaging signal.

In some embodiments, the first optical signal an RGB imaging signal, and wherein the second optical signal a laser speckle imaging signal. In some embodiments, the first imaging unit and the second imaging unit have different imaging modalities. In some embodiments, the different imaging modalities comprise at least one imaging modality selected from the group consisting of an infrared imaging sensor for laser speckle imaging, a fluorescence imaging sensor for fluorescence imaging, a mosaic sensor for hyperspectral imaging, a short wave infrared (SWIR) sensor for SWIR imaging, and a depth sensor for depth imaging.

In some embodiments, the imaging device further comprises an image processor operatively coupled to the first imaging unit, the second imaging unit, or both, wherein the image processor is configured to process one or more images obtained using the first imaging unit, the second imaging unit, or both. In some embodiments, the one or more images comprise one or more images of a surgical scene, and wherein the image processor is configured to produce a visualization of a surgical scene. In some embodiments, the visualization of the surgical scene comprises a dynamic overlay of images. In some embodiments, the dynamic overlay of images comprises one or more imaging modalities, the one or more imaging modalities selected from the group consisting of: a laser speckle image, a depth image, a fluorescence image, and an RGB image of the surgical scene. In some embodiments, the dynamic overlay of images is adjustable based on a user input or selection of a desired imaging modality. In some embodiments, the imaging device comprises a portion of a laparoscope or an endoscope.

In some embodiments, a field of view of an image from the first imaging unit, the second imaging unit, or both comprises a marker configured to aid in positioning or alignment the first imaging unit relative to the second imaging unit. In some embodiments, the marker comprises a notch. In some embodiments, the marker comprises a fiducial marker. In some embodiments, the elongated optical path comprises one or more obstructions between one or more pairs of lenses, and wherein the one or more obstructions appear in the field of view as the marker. In some embodiments, the imaging device further comprises an optical source configured to project one or more visual references onto the surgical scene, and wherein the one or more visual references appear in the field of view as the marker. In some embodiments, the elongated optical path comprises one or more lenses for adjusting a field of view or an angle of view of the surgical scene. In some embodiments, the elongated optical path comprises one or more rod lenses or objective assemblies.

In some embodiments, the imaging module comprises one or more buttons for receiving a physical input from a user. In some embodiments, the physical input controls an operation of the first imaging unit; the second imaging unit; a processor coupled to the first imaging unit, the second imaging unit, or both; or any combination thereof. In some embodiments, the elongated portion of the housing is rotatable relative to the first imaging unit. In some embodiments, the housing comprises an eyepiece. In some embodiments, the elongated portion of the housing comprises one or more optical filters. In some embodiments, the one or more optical filters comprises a notch filter comprising an absorption band at an excitation wavelength for fluorescence imaging. In some embodiments, the beam splitter is a dichroic beam splitter. In some embodiments, the imaging device does not comprise a window or an eyepiece between the elongated portion of the housing and the beam splitter. In some embodiments, a focus of the first optical signal on the first imaging unit is fixed during manufacturing. In some embodiments, a focus of the first optical signal on the first imaging unit is substantially not adjustable by a user.

In another aspect, the present disclosure provides a system comprising the imaging device of any aspect or embodiment and the second imaging unit, wherein the second imaging unit is releasably attached to the imaging device. In some embodiments, the first imaging unit is rotatable relative to the second imaging unit, the elongated portion of the housing, or both.

In another aspect, the present disclosure provides an imaging device. The imaging device may comprise: a housing; an insertion portion of housing, the insertion portion having an elongated optical axis, wherein a first optical signal and a second optical signal are transmitted along the elongated optical axis, wherein the first optical signal and the second optical signal each comprise a distinct wavelength range; a beam splitter configured to deliver the first optical signal to the first imaging unit and configured to deliver the second optical signal to a second imaging unit; one or more markers along the elongated optical axis; and a focusing knob coupled to a lens on an optical path of either of the first imaging unit or the second imaging unit, wherein adjustment of the focusing knob is configured to bring an image of the one or more markers into focus on both of the first imaging unit and the second imaging unit.

In some embodiments, the housing comprising the first imaging unit is hermetically sealed. In some embodiments, the first imaging unit, the second imaging unit, or both comprises an imaging sensor. In some embodiments, the imaging sensor comprises an infrared sensor. In some embodiments, the first imaging unit, the second imaging unit, or both comprises a camera or a sensor for RGB imaging. In some embodiments, the first optical signal has a first range of wavelengths and the second optical signal has a second range of wavelengths. In some embodiments, the first range of wavelengths is greater than a threshold wavelength and the second range of wavelengths is less than the threshold wavelength. In some embodiments, the threshold wavelength is between about 700 nanometers (nm) to about 800 nm.

In some embodiments, the first optical signal a laser speckle imaging signal, and wherein the second optical signal an RGB imaging signal. In some embodiments, the first optical signal an RGB imaging signal, and wherein the second optical signal a laser speckle imaging signal. The first imaging unit and the second imaging unit have different imaging modalities. In some embodiments, the different imaging modalities comprise at least one imaging modality selected from the group consisting of an infrared imaging sensor for laser speckle imaging, a fluorescence imaging sensor for fluorescence imaging, a mosaic sensor for hyperspectral imaging, a short wave infrared (SWIR) sensor for SWIR imaging, and a depth sensor for depth imaging.

In some embodiments, the imaging device further comprises an image processor operatively coupled to the first imaging unit, the second imaging unit, or both, wherein the image processor is configured to process one or more images obtained using the first imaging unit, the second imaging unit, or both. In some embodiments, the one or more images comprise one or more images of a surgical scene, and wherein the image processor is configured to produce a visualization of a surgical scene. In some embodiments, the visualization of the surgical scene comprises a dynamic overlay of images. In some embodiments, the dynamic overlay of images comprises one or more imaging modalities, the one or more imaging modalities selected from the group consisting of: a laser speckle image, a depth image, a fluorescence image, and an RGB image of the surgical scene. In some embodiments, the dynamic overlay of images is adjustable based on a user input or selection of a desired imaging modality. In some embodiments, the imaging device comprises a portion of a laparoscope or an endoscope.

In some embodiments, a field of view of an image from the first imaging unit, the second imaging unit, or both comprises a marker configured to aid in positioning or alignment the first imaging unit relative to the second imaging unit. In some embodiments, the marker comprises a notch. In some embodiments, the marker comprises a fiducial marker. In some embodiments, the elongated optical path comprises one or more obstructions between one or more pairs of lenses, and wherein the one or more obstructions appear in the field of view as the marker. In some embodiments, the imaging device further comprises an optical source configured to project one or more visual references onto the surgical scene, and wherein the one or more visual references appear in the field of view as the marker.

In some embodiments, the elongated optical path comprises one or more lenses for adjusting a field of view or an angle of view of the surgical scene. In some embodiments, the elongated optical path comprises one or more rod lenses or objective assemblies. In some embodiments, the imaging module comprises one or more buttons for receiving a physical input from a user. In some embodiments, the physical input controls an operation of the first imaging unit; the second imaging unit; a processor coupled to the first imaging unit, the second imaging unit, or both; or any combination thereof. In some embodiments, the elongated portion of the housing is rotatable relative to the first imaging unit. In some embodiments, the coupling portion comprises an eyepiece. In some embodiments, the elongated portion of the housing comprises one or more optical filters. In some embodiments, the one or more optical filters comprises a notch filter comprising an absorption band at an excitation wavelength for fluorescence imaging.

In some embodiments, the beam splitter is a dichroic beam splitter. In some embodiments, the imaging device does not comprise a window or an eyepiece between the elongated portion of the housing and the beam splitter. In some embodiments, a focus of the first optical signal on the first imaging unit is fixed during manufacturing. In some embodiments, a focus of the first optical signal on the first imaging unit is substantially not adjustable by a user.

In another aspect, the present disclosure provides a system comprising the imaging device of any aspect or embodiment and the second imaging unit, wherein the second imaging unit is releasably attached to the imaging device. In some embodiments, the first imaging unit is rotatable relative to the second imaging unit, the elongated portion of the housing, or both. In some embodiments, the fiducial marker comprises a first set of fiducial marks and a second set of fiducial marks.

In some embodiments, the first set of fiducial marks can have more fine or narrow notches as compared to the second set of fiducial marks. In some embodiments, the user can use differences in resolution of the notches between the first set of fiducial marks and the second set of fiducial marks to determine an adjustment needed to come into focus. In some embodiments, the image processor is configured to determine an adjustment needed to come into focus based on the differences in fiducial marks.

In another aspect, the present disclosure provides a system. The system may comprise an imaging device comprising a distal end for providing a field of view of a surgical scene and a proximal end that is releasably attachable to an external imaging unit, wherein the imaging device comprises an internal imaging unit that is (i) integrated with the scope and (ii) disposed between the proximal end of the scope and the distal end of the scope, and wherein the external imaging unit comprises at least one imaging sensor and one or more optical elements for directing a first optical signal to the internal imaging unit and a second optical signal to the external imaging unit to which the imaging device is releasably attached.

In another aspect, the present disclosure provides a method of imaging a target site, the method comprising: providing the imaging device or the system of any of aspect or embodiment.

In another aspect, the present disclosure provides a method of imaging a target site. The method may comprise receiving a first optical signal and a second optical signal from the target site wherein the first optical signal and the second optical signal each comprise a distinct wavelength range; directing the first optical signal to a first imaging unit, wherein the first imaging unit is integrated within a housing of a laparoscope or an endoscope; coupling a second imaging unit to the laparoscope or the endoscope; and directing the second optical signal to the second imaging unit.

In some embodiments, the method further comprises adjusting a focus of the second optical signal on the second imaging unit. In some embodiments, the method further comprises adjusting an orientation of the first imaging unit relative to the second imaging unit. In some embodiments, the adjusting comprises rotating the first imaging unit relative to an insertion portion of the laparoscope or the endoscope.

In another aspect, the present disclosure provides a system comprising a scope with a distal end for providing a field of view of a surgical scene and a proximal end that is releasably attachable to an imaging unit. The imaging unit may comprise a camera or a sensor for RGB/white light imaging of the surgical scene.

In some embodiments, the scope may comprise an imaging module that is (i) integrated with the scope and (ii) disposed between the proximal end of the scope and the distal end of the scope. In some embodiments, the imaging module comprises at least one imaging sensor and one or more optical elements for directing one or more optical signals to the at least one imaging sensor of the imaging module and the imaging unit to which the scope is releasably attached. In some embodiments, the at least one imaging sensor may comprise an infrared sensor.

In some embodiments, the one or more optical elements may be configured to direct (i) a first set of light signals to the at least one sensor of the imaging module and (ii) a second set of light signals to the imaging unit. In some embodiments, the first set of light signals have a first range of wavelengths and the second set of light signals have a second range of wavelengths. In some embodiments, the first range of wavelengths is greater than a threshold wavelength and the second range of wavelengths is less than the threshold wavelength. In some embodiments, the threshold wavelength is between about 700 nanometers (nm) to about 800 nm. In some embodiments, the first set of light signals is usable for laser speckle imaging, and the second set of light signals is usable for RGB imaging.

In some embodiments, the at least one imaging sensor comprises two or more imaging sensors having different imaging modalities. In some embodiments, the two or more imaging sensors may comprise, for example, an infrared imaging sensor for laser speckle imaging, a fluorescence imaging sensor for fluorescence imaging, and/or a depth sensor for depth imaging.

In some embodiments, the one or more optical elements may be configured to direct (i) a first set of light signals to a first sensor of the two or more imaging sensors and (ii) a second set of light signals to a second sensor of the two or more imaging sensors. In some embodiments, the first set of light signals have a first range of wavelengths and the second set of light signals have a second range of wavelengths. In some embodiments, the first range of wavelengths is greater than a threshold wavelength and the second range of wavelengths is less than the threshold wavelength.

In some embodiments, the system may further comprise an image processor operatively coupled to the at least one sensor and the imaging unit. The image processor may be configured to process one or more images obtained using the at least one sensor and/or the imaging unit to generate a visualization of the surgical scene. In some embodiments, the visualization of the surgical scene comprises a dynamic overlay of images. In some embodiments, the dynamic overlay of images comprises a laser speckle image, a depth image, a fluorescence image, and/or an RGB image of the surgical scene. In some embodiments, the dynamic overlay of images is adjustable based on a user input or selection of a desired imaging modality.

In some embodiments, the scope comprises a laparoscope or an endoscope. In some embodiments, the field of view provided by the scope may comprise a marker to aid in positioning or alignment of the scope relative to one or more features or regions of the surgical scene. In some embodiments, the marker may comprise a notch. In some embodiments, the scope may comprise one or more lenses for adjusting a field of view or an angle of view of the surgical scene. In some embodiments, the scope may comprise one or more rod lenses or objective assemblies disposed within an elongated portion of the scope.

In some embodiments, the imaging module may comprise one or more buttons for receiving a physical input from a user. In some embodiments, the physical input may be used to control an operation of the imaging module or an image processor operatively coupled to the imaging module or the imaging unit.

In some embodiments, a first portion of the scope may be rotatable relative to a second portion of the scope. In some embodiments, the scope may be configured to rotate relative to the imaging module.

Another aspect of the present disclosure provides a system comprising one or more computer processors and computer memory coupled thereto. The computer memory comprises machine executable code that, upon execution by the one or more computer processors, implements any of the methods above or elsewhere herein.

Additional aspects and advantages of the present disclosure will become readily apparent to those skilled in this art from the following detailed description, where only illustrative embodiments of the present disclosure are shown and described. As will be realized, the present disclosure is capable of other and different embodiments, and its several details are capable of modifications in various obvious respects, all without departing from the disclosure. Accordingly, the drawings and description are to be regarded as illustrative in nature, and not as restrictive.

INCORPORATION BY REFERENCE

All publications, patents, and patent applications mentioned in this specification are herein incorporated by reference to the same extent as if each individual publication, patent, or patent application was specifically and individually indicated to be incorporated by reference. To the extent publications and patents or patent applications incorporated by reference contradict the disclosure contained in the specification, the specification is intended to supersede and/or take precedence over any such contradictory material.

BRIEF DESCRIPTION OF THE DRAWINGS

The novel features of the invention are set forth with particularity in the appended claims. A better understanding of the features and advantages of the present invention will be obtained by reference to the following detailed description that sets forth illustrative embodiments, in which the principles of the invention are utilized, and the accompanying drawings (also "Figure" and "FIG." herein), of which:

DETAILED DESCRIPTION

Figures 1A, 1B:
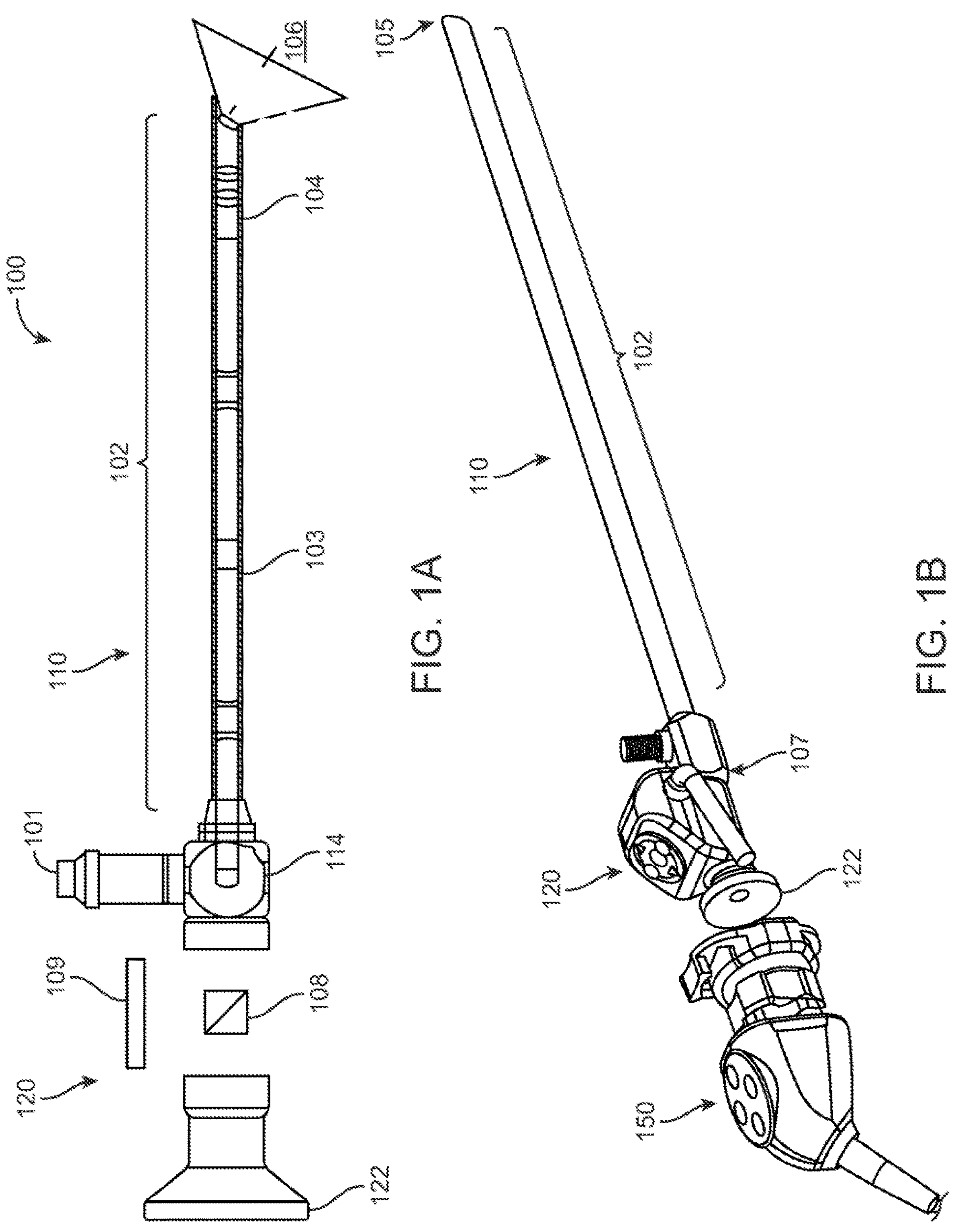
FIG. 1A and FIG. 1B schematically illustrate various exemplary configurations for the imaging systems of the present disclosure.

While various embodiments of the invention have been shown and described herein, it will be obvious to those skilled in the art that such embodiments are provided by way of example only. Numerous variations, changes, and substitutions may occur to those skilled in the art without departing from the invention. It should be understood that various alternatives to the embodiments of the invention described herein may be employed.

Whenever the term "at least," "greater than," or "greater than or equal to" precedes the first numerical value in a series of two or more numerical values, the term "at least," "greater than" or "greater than or equal to" applies to each of the numerical values in that series of numerical values. For example, greater than or equal to 1, 2, or 3 is equivalent to greater than or equal to 1, greater than or equal to 2, or greater than or equal to 3.

Whenever the term "no more than," "less than," or "less than or equal to" precedes the first numerical value in a series of two or more numerical values, the term "no more than," "less than," or "less than or equal to" applies to each of the numerical values in that series of numerical values. For example, less than or equal to 3, 2, or 1 is equivalent to less than or equal to 3, less than or equal to 2, or less than or equal to 1.

Certain inventive embodiments herein contemplate numerical ranges. When ranges are present, the ranges include the range endpoints. Additionally, every sub range and value within the range is present as if explicitly written out. The term "about" or "approximately" may mean within an acceptable error range for the particular value, which will depend in part on how the value is measured or determined, e.g., the limitations of the measurement system. For example, "about" may mean within 1 or more than 1 standard deviation, per the practice in the art. Alternatively, "about" may mean a range of up to 20%, up to 10%, up to 5%, or up to 1% of a given value. Where particular values are described in the application and claims, unless otherwise stated the term "about" meaning within an acceptable error range for the particular value may be assumed.

The term "perfusion," as used herein, generally refers to passage of fluid through the circulatory system or lymphatic system to an organ or a tissue. In an example, perfusion may refer to the delivery of blood at the level of the arteries or capillaries, in which exchange of oxygen and/or nutrients between blood and tissue takes place. In some cases, perfusion may comprise flow rate of the fluid, volume of the fluid that is present or traversing across a target tissue site, a pattern of flow channels of the fluid at the target tissue site, or a combination thereof. In some cases, perfusion of the liquid of interest may be increasing, decreasing, or remaining substantially the same during one or more imaging processes. In some cases, any change in flow rate or volume of the perfusing fluid may be indicative of (i) one or more biological events or (ii) one or more surgical events occurring upstream of, downstream of, or substantially at the target tissue site. When quantified, perfusion may be measured as the rate at which blood is delivered to tissue, or volume of blood per unit time (blood flow) per unit tissue mass, in units of cubic meter per second per kilogram ($m^3/s/kg$) or milliliters per minute per grams (mL/min/g). A degree of perfusion may be indicative of one or more health conditions, e.g., cardiovascular disease such as coronary artery disease, cerebrovascular disease, peripheral artery disease, etc.

The term "real time" or "real-time," as used interchangeably herein, generally refers to an event (e.g., an operation, a process, a method, a technique, a computation, a calculation, an analysis, a visualization, an optimization, etc.) that is performed using recently obtained (e.g., collected or received) data. In some cases, a real time event may be performed almost immediately or within a short enough time span, such as within at least 0.0001 millisecond (ms), 0.0005 ms, 0.001 ms, 0.005 ms, 0.01 ms, 0.05 ms, 0.1 ms, 0.5 ms, 1 ms, 5 ms, 0.01 seconds, 0.05 seconds, 0.1 seconds, 0.5 seconds, 1 second, or more. In some cases, a real time event may be performed almost immediately or within a short enough time span, such as within at most 1 second, 0.5 seconds, 0.1 seconds, 0.05 seconds, 0.01 seconds, 5 ms, 1 ms, 0.5 ms, 0.1 ms, 0.05 ms, 0.01 ms, 0.005 ms, 0.001 ms, 0.0005 ms, 0.0001 ms, or less.

The present disclosure provides systems and methods for medical imaging. A system may allow visualization of structures or features (e.g., blood flow) that are in a target site, near a target site, and/or beneath the surface of a target site, which structures or features would ordinarily be invisible to the human eye or other imaging systems. Imaging devices and systems of the present disclosure may allow visualization of one or more anatomical structures and/or physiological features or functions. Imaging devices and systems of the present disclosure may be used for physiologic, pathologic, morphologic, and/or anatomic visualizations of various structures, features, and/or functions within a subject's body. Imaging devices and systems of the present disclosure may make the invisible, visible. Imaging devices and systems of the present disclosure may help visualize the invisible. A system may enable a plurality of different imaging modalities. For example, the system may provide speckle imaging capabilities as well as photographic images and/or video in a single embodiment. In such case, the system may allow users to switch between different visualization modes, e.g., (i) white-light (RGB) based video only, (ii) laser speckle imaging only, (iii) fluorescence imaging, (iv) depth imaging, (v) a mosaic sensor for hyperspectral imaging, (vi) a short wave infrared (SWIR) sensor for SWIR imaging, and (vii) any combination of white-light based video, laser speckle imaging, fluorescence imaging, a mosaic sensor for hyperspectral imaging, a short wave infrared (SWIR) sensor for SWIR imaging, and/or depth imaging.

Imaging devices and systems of the present disclosure may allow visualization of perfusion (e.g., blood perfusion) at a tissue site of interest substantially in real-time, as compared to delayed visualization of perfusion data from dye-based angiography. In an example, a real-time event may comprise visualization of blood perfusion at a tissue site, in which a data set (e.g., one or more light signals) indicative of the blood perfusion is captured by a tool (e.g., an image sensor), and the data is transmitted to a display for visualization to a user. In another example, a real-time event may comprise combining two different data sets that are indicative of different features of the tissue site for a simultaneous visualization at the display. Imaging devices and systems of the present disclosure may be usable for a number of medical applications, e.g., general surgery, neurosurgical procedures, orthopedic procedures, and spinal procedures. Imaging devices and systems of the present disclosure may be applicable to a wide variety of endoscopy-based procedures, including, but are not limited to, cholecystectomy (e.g., 1,200,000 procedures per year), hysterectomy (e.g., 575,000 procedures per year), thyroidectomy (e.g., 150,500 procedures per year), and gastrectomy (e.g., 225,000 procedures per year).

In some cases, the entirety of the system may be configured to be reused. In some cases, at least a portion of the system may be configured to be reused. In some cases, the system may be a disposable unit.

FIG. 1A shows an exemplary embodiment of the imaging system including an imaging module 120 and a scope 110. In some embodiments, the scope 110 has an elongated body 102 comprising one or more optical elements including a set of lenses 103, an optical assembly 104, a light post 101, and a block 114 where the imaging module 120 can couple. In some cases, light may enter the system through the light post 101 and be transmitted through fibers or the one or more optical elements within the elongated body of the scope to the distal end 105 of the scope 110. The light may be directed onto a surgical scene within the field of view or angle of view 106 of the system. The distal end 105 of the scope 110 may then capture optical signals that are sourced (e.g., reflected or generated) from the surgical scene. The one or more optical elements within the elongated body of the scope may transmit the optical signals reflected or generated from the surgical scene towards the proximal end of imaging device 100. FIG. 1B shows another rendering of the embodiment of FIG. 1A. The imaging device 100 may comprise a beam splitter 108, which may be configured to direct (i) a first portion of the optical signals to the imaging module 120, e.g., to an infrared sensor 109 within the imaging module, and (ii) a second portion of the optical signals to an aperture at the proximal end of the imaging device 100. At the proximal end of the imaging device 100, the system may comprise an eyepiece 122, 222, 622 and/or an imaging unit 150, 250, 350 releasably coupled to the proximal end of the imaging device. (See also, FIGS. 2, 3A-3C, 6A, and 6B).

In some cases, imaging module 120 can be hermetically sealed to the scope 110. Thus, the imaging system may represent a single hermetically sealed and sterilizable assembly that may not be disassembled by the user. There are several benefits of preventing users from assembling the imaging module 120 and the scope 110. For example, the optical path from a scope to the imaging device may fixed thus reducing a need to focus or align. For example, a hermetic seal may prevent fogging or moisture leaks into the optical assembly during use and/or during sterilization. In an example, the imaging module 120 can be hermetically sealed to the scope 110 using a seal 107.

Figure 2:
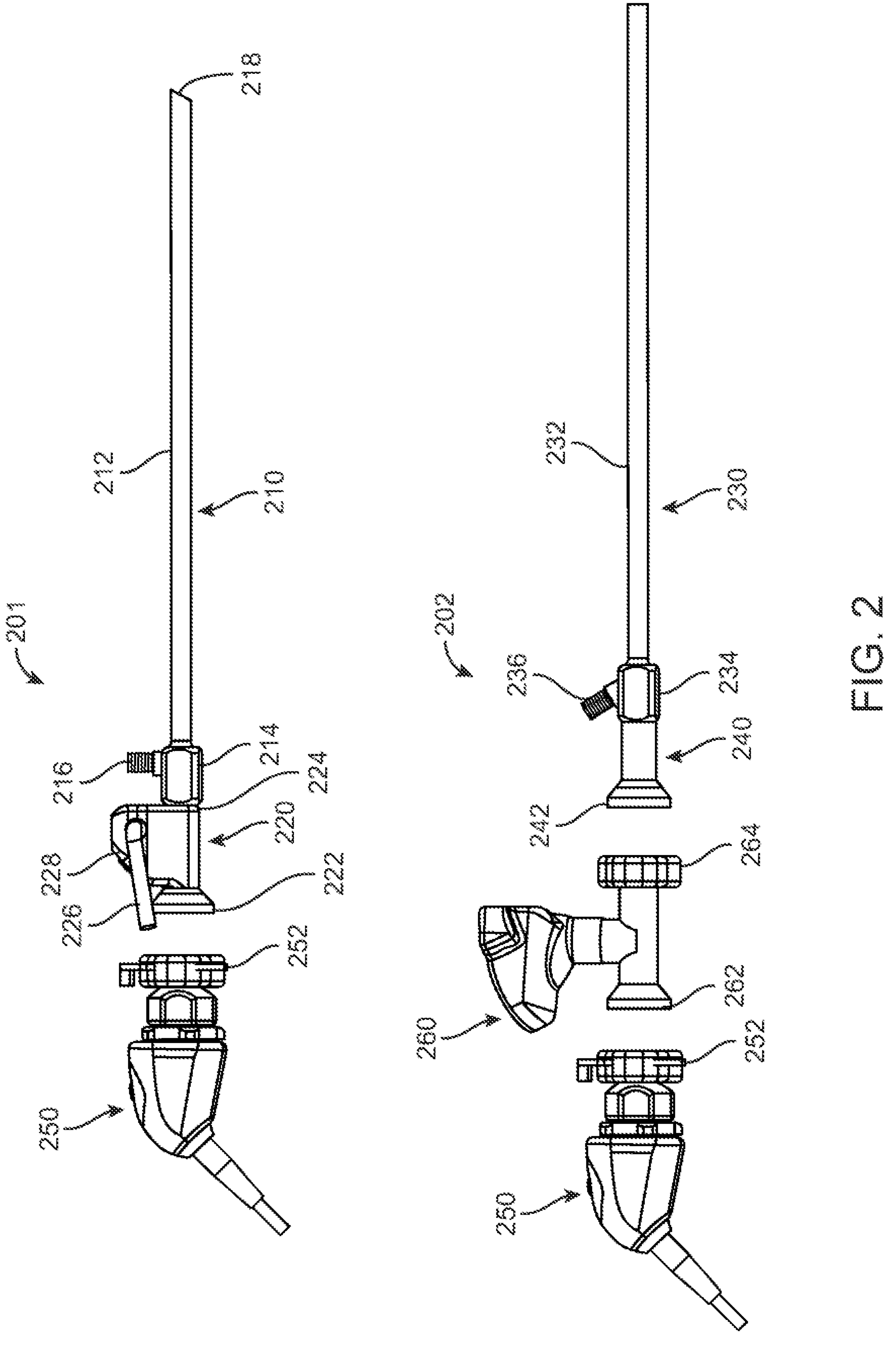
FIG. 2 shows a reduced footprint of the presently disclosed imaging systems compared to other commercially available imaging systems, in accordance with some embodiments.

FIG. 2 shows a reduced footprint of a system of the present disclosure as compared to other commercially available imaging systems. A system 202 having an independent imaging module 260 and scope 230 having an eyepiece 240 may result in a larger footprint than the integrated scope system 201 of the present disclosure. The decreased footprint of the integrated scope system 201 is advantageous in a surgical setting, where space in an operating room is valuable and limited. Additionally, the reduced footprint of the integrated scope system of the present disclosure makes the entire integrated scope system easier to handle and more easily maneuverable. Furthermore, the integrated scope system 201 may provide a more consistent medical imaging experience compared to other conventional imaging systems, which may require additional calibration in order to account for differences in the physical dimensions or characteristics of third-party scopes and cameras. Additionally, a system comprised of independent components may require the user to manually adjust focus of the infrared (IR) sensor to compensate for variability in the scopes that may be attached. For example, in the traditional system 202, the distal end of the independent imaging module 260 must be assembled to the proximal end of the traditional scope 230. This requires a separate alignment and focusing step in addition to alignment and focusing of the system 202 to an imaging unit 250. In an example, an interface ring 252 on a distal end of the imaging unit 250 could be used to secure the system 202 to an imaging unit 250.

In the present disclosure, an integrated scope system may allow a fixed-focus imaging module with an IR sensor, thus reducing the burden on the user during initial setup of the imaging system. In an example, an integrated scope system 201 includes a scope 210 and imaging module 220. In an example, the scope 201 includes an elongate body 212, a scope block 214, a light post 216, and a distal end of the scope 218. In an example, an imaging module 220 can include an eyepiece 222, a user interface 228, and a hermetic interface 224. In an example, the eyepiece 222 is configured to secure to interface ring 252 of the imaging unit 250. In an example, the hermetic interface 224 is configured to interface with a proximal end of the scope 210.

In some cases, an imaging device 201 can comprise a housing and an insertion portion of housing. The insertion portion may have an elongated optical axis. A first optical signal and a second optical signal may be transmitted along the elongated optical axis. In some cases, the first optical signal and the second optical signal each may comprise a distinct wavelength range.

In some cases, an imaging module portion may comprise a first housing that is coupled to a second housing of a scope portion. In an example, the scope 210 and the imaging module 220 portions can form a unitary housing. In an example, the imaging device 201 can further comprise a housing coupling configured to align one or more optical elements of the scope 210 and imaging module 220 when their first and second housing portions are joined. In an example, objective adaptor 510, 610 described below can serve as a housing coupling.

In some cases, any of the imaging devices disclosed herein including imaging device 201 can comprise a first imaging unit integrated within the housing, a beam splitter configured to deliver the first optical signal to the first imaging unit and configured to deliver the second optical signal to a second imaging unit, and a coupling portion along an axis of the second optical signal, where the coupling portion is configured to releasably couple the second imaging unit to the housing. In an example, the first imaging unit can be the imaging module 120, 220, 320. In an example, the second imaging unit can be the imaging unit 150, 250, 350. In some cases, the coupling portion can be configured to form a portion of the housing. In an example, the coupling portion comprises an eyepiece 122, 222, 622 (see, e.g., FIGS. 1A-1B, 2, 6A and 6B). In an example, the coupling portion can be a coupling portion 624 positioned between the eyepiece 622 and focusing device 640.

In some cases, the integrated scope system 201 or imaging device does not comprise a window or an eyepiece between the elongated portion of the housing and the beam splitter.

In some cases, a focus of the first optical signal on the first imaging unit is fixed during manufacturing. In some cases, this can be a benefit to the user in that they do not need to adjust the focus of disjoint components. In an example, the focus of the first optical signal on the first imaging unit is substantially not adjustable by a user.

Figure 3A:
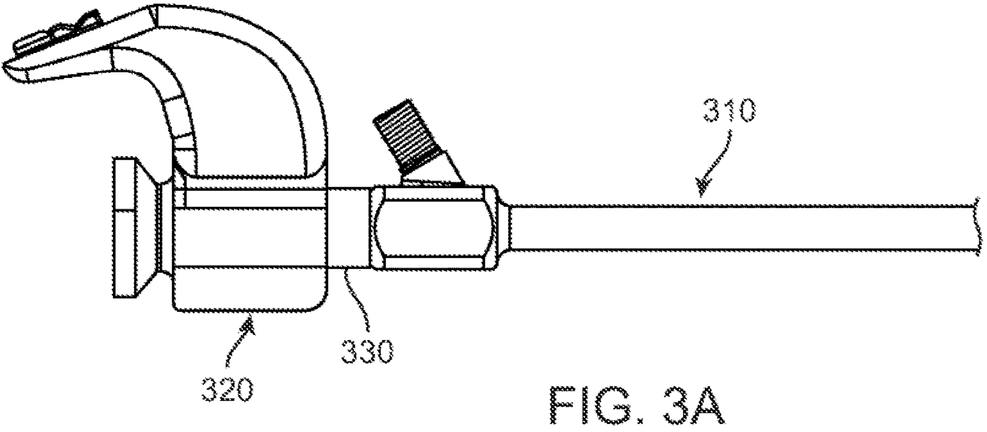
FIGS. 3A-3D illustrate different embodiments of an imaging system such that a first portion of the scope or system can rotate relative to a second portion of the scope or system, in accordance with some embodiments.
Figure 3B:
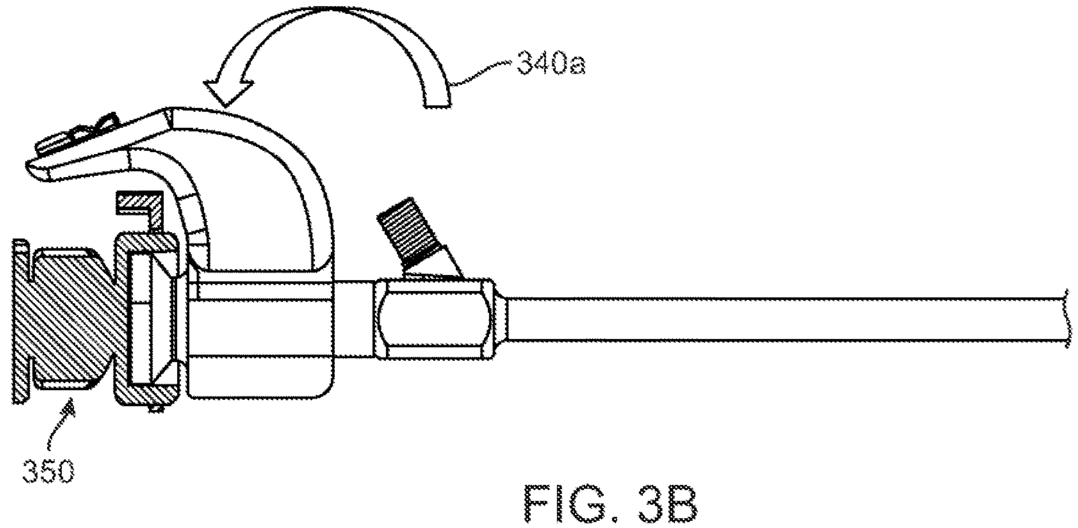
Figure 3C:
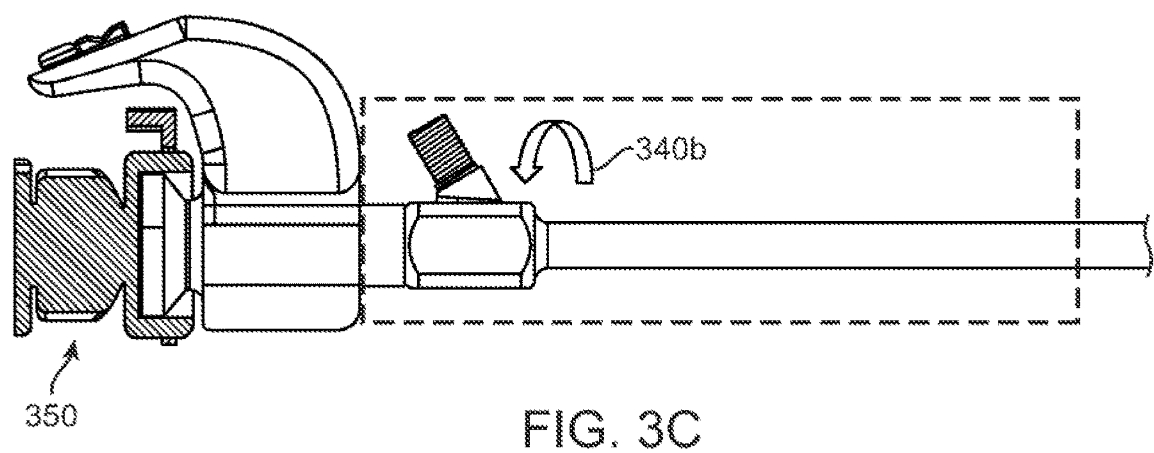
Figure 3D:
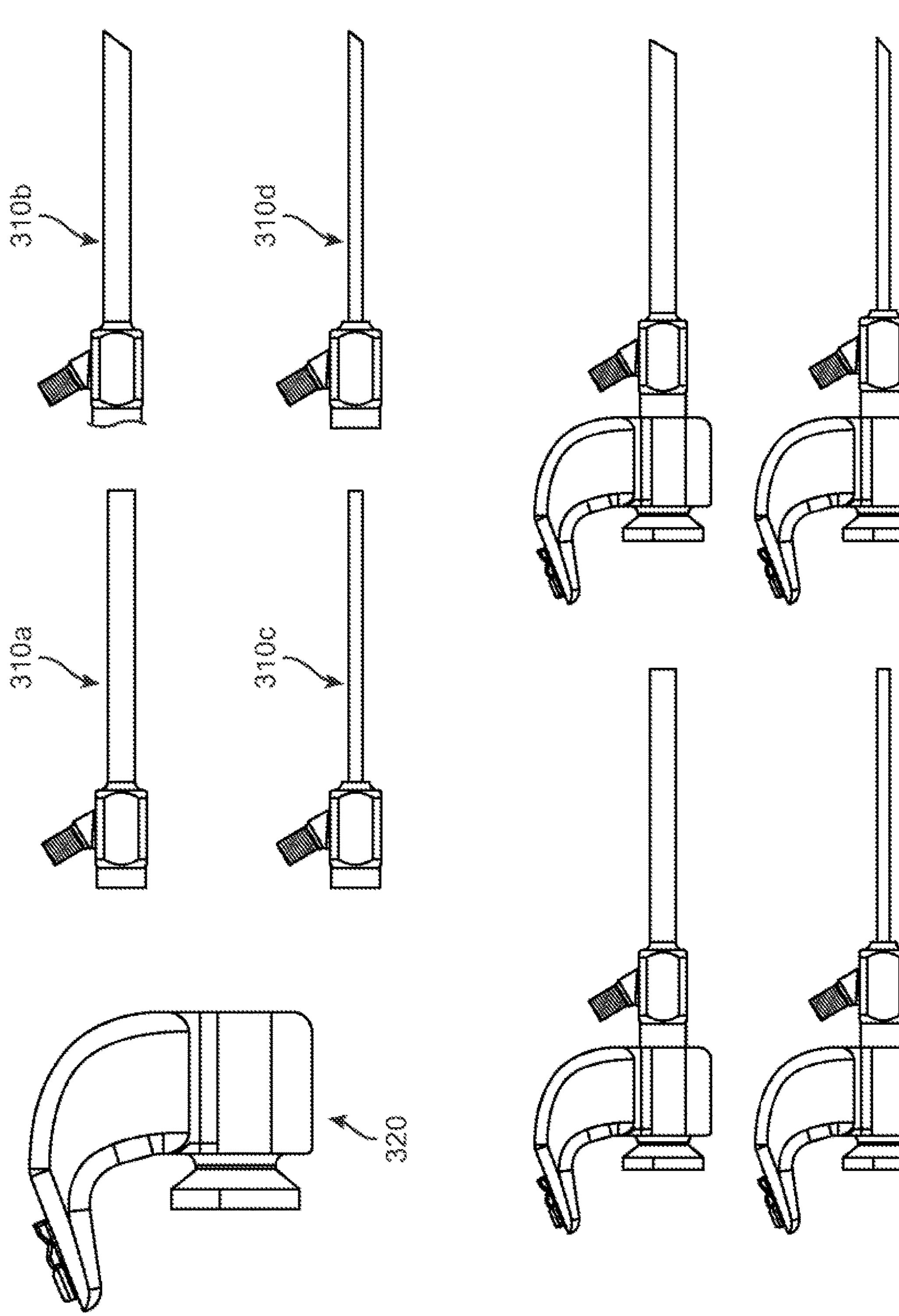

In some cases, the second imaging unit can be releasably attached to the imaging device (see FIGS. 3C and 3D). In some cases, the first imaging unit can be rotatable relative to the second imaging unit, the elongated portion of the housing, or both.

Figure 5A:
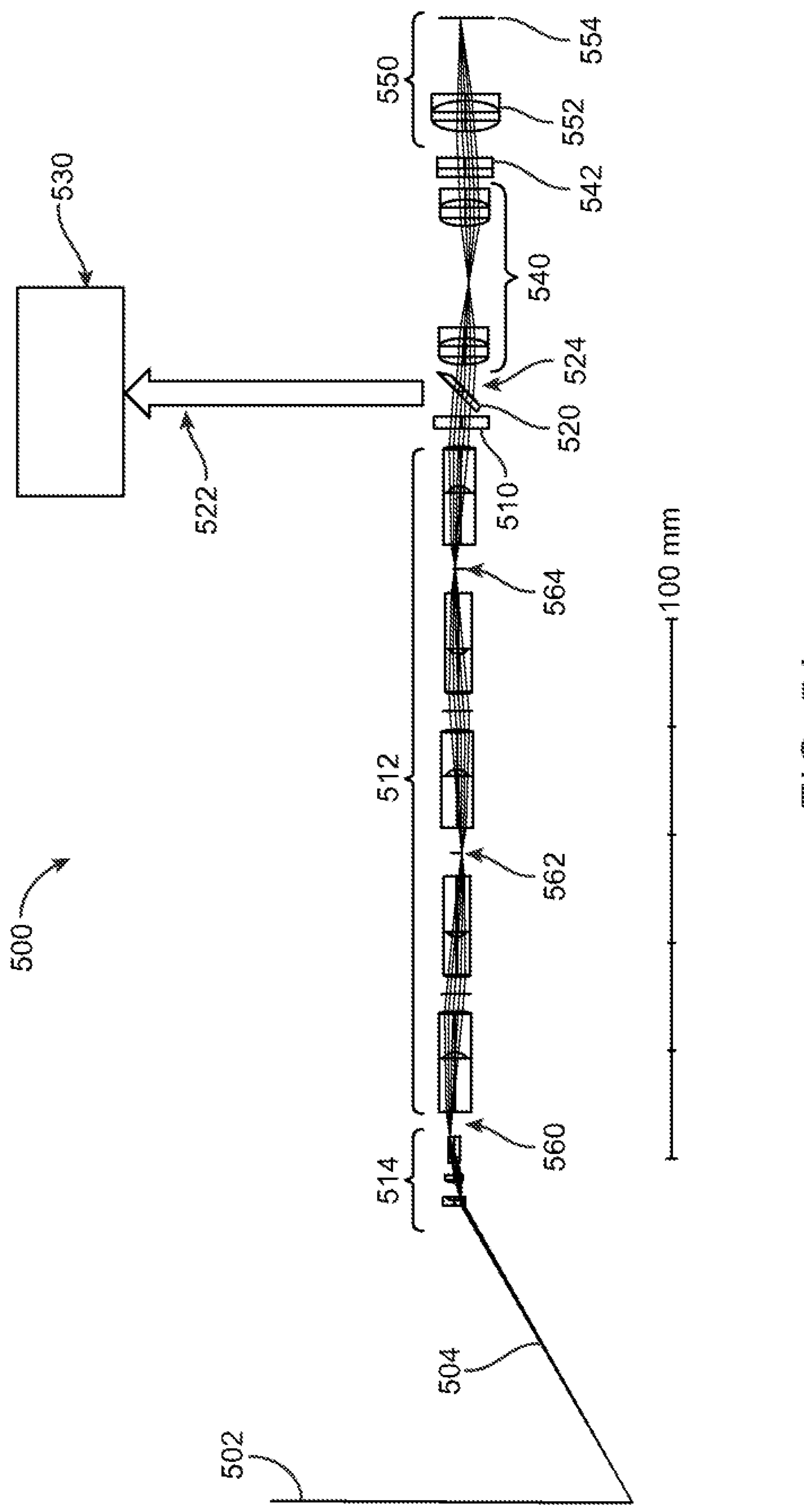
FIGS. 5A-5D illustrate integration of fiducials and optical elements of an integrated scope system directing optical signals from a surgical scene, in accordance with some embodiments.

In an example, the first optical signal can be a first portion of optical signals 522 from a surgical scene 502 to an imaging module 530 and the second optical signal can be a second portion of optical signals 524 to a pupil relay lens set 540 (see, e.g., FIG. 5A). In some cases, the optical axis forms an optical path for light. In some cases, optical signals 524 are emitted from the eyepiece 620.

In some cases, the housing can be hermetically sealed. In an example, the hermetically sealed housing can protect the first imaging unit and/or prevent fogging of the optical path. In some cases, the elongated portion of the housing comprises one or more optical filters. Examples of optical filters include but are not limited to a notch filter comprising an absorption band at an excitation wavelength for fluorescence imaging (e.g., notch block filter 536) and an RGB block filter 534 (see, FIGS. 5C and 5D), RGB pass filter, a low pass filter, a high pass filter, or another filter such as might be useful to remove unwanted light such as light from a laser of the present disclosure.

In some cases, any imaging device described herein may comprise a housing, and an insertion portion of housing. The insertion portion of the housing may have an elongated optical axis, where a first optical signal and a second optical signal are transmitted along the elongated optical axis. In some cases, the first optical signal and the second optical signal each comprise a distinct wavelength range. In some cases, the insertion portion comprises an even number of pairs of lenses and an unpaired lens. In some cases, any beam splitter described herein can be positioned distal to the insertion portion configured to deliver the first optical signal to a first imaging unit and configured to deliver the second optical signal to a second imaging unit. In some cases, any imaging device described herein may further comprise a lens along a first imaging axis distal to the beam splitter, where an image distal to the lens on the first imaging portion is inverted, and a pair of lenses and an unpaired lens on a second imaging axis distal to the beam splitter, where an image distal to the unpaired lens on the second imaging axis is right-side-up. (See, e.g., FIGS. 5A-5B, and FIG. 9)

In some cases, the system may comprise a scope. The scope may comprise a distal end for providing a field of view of a surgical scene and a proximal end. The proximal end of the scope may be configured to be releasably attachable to an imaging unit (e.g., a camera). The imaging device may be configured to visualize one or more external and/or inner surfaces of a tissue (e.g., skin or internal organ) of a subject. The imaging device may be used to examine (e.g., visually examine) the tissue of the subject. The scope may be used to diagnose and/or assist in a medical intervention (e.g., treatments, such as surgery). In some cases, the imaging device may comprise or be configured for use as a laparoscope or an endoscope. Examples of the endoscope may include, but are not limited to, a cystoscope (bladder), nephroscope (kidney), bronchoscope (bronchus), arthroscope (joints) and colonoscope (colon), and laparoscope (abdomen or pelvis).

The scope may allow a user (e.g., a medical practitioner such as a physician, nurse practitioner, nurse, imaging specialist, etc.) to visualize and/or analyze a target site of a subject, such as an internal tissue of a patient.

The scope may comprise an elongated body with a hollow region inside. The scope and elongated body may be configured to transmit one or more optical signals (e.g., a light beam, light signal, coherent laser light, backscattered light, white light, reflected light, etc.). The scope may be configured to transmit at least 1, 2, 3, 4, 5, 6, 7, 8, 9, 10, or more optical signals. The one or more optical signals may comprise a light beam. The one or more optical signals may comprise a single light beam from a single light source. Alternatively, the one or more optical signals may comprise a combined light beam comprising a plurality of light beams. In some cases, the plurality of light beams may be directed to the target site from the same direction. Alternatively, the plurality of light beams may be directed to the target site from different directions. In some cases, the plurality of light beams may comprise (i) a white light and (ii) one or more laser beams. The plurality of light beams may originate from a single optical source or a plurality of optical sources. The one or more laser beams may include at least 1, 2, 3, 4, 5, 6, 7, 8, 9, 10, or more laser beams. The one or more laser beams may include at most 10, 9, 8, 7, 6, 5, 4, 3, 2, or 1 laser beam.

Laser beams of varying wavelengths may be selected based on a desired penetration depth of the tissue site. Alternatively, or in addition to, laser beams of varying wavelengths may be selected based on a composition of interest (e.g., one or more molecules, compounds, or chemicals) present or expected to be present at the tissue site. In an example, a first laser beam having a first wavelength may be selected for detecting oxygenated blood, whereas a second laser beam having a second wavelength may be selected for detecting de-oxygenated blood. A user of the subject systems and methods provided herein may be able to select one or more laser wavelengths of interest depending on such parameters of the tissue site.

The scope may be configured to receive one or more optical signals from an illumination source. In an example, the illumination source can be light post 101, 216 (see, e.g., FIG. 1A and FIG. 2). The scope may be configured to direct the one or more optical signals onto the target site of the subject's body. The optical signals may comprise light signals. One or more of the optical signals may be reflected from a target site within a subject's body. The one or more light signals may be reflected or emitted from the target site upon exposure to or illumination of the target site by an optical beam. The scope may be configured to (1) receive a light beam from an illumination source and (2) direct the light beam onto the target site of the subject's body. In some cases, the scope may be configured to (1) receive a combined light beam from the illumination source and (2) direct the combined light beam onto the target site within the subject's body. In some examples, a natural tissue of the target site or one or more dyes introduced to the target site may be responsible for reflecting or emitting the one or more optical signals. Alternatively, or in addition to, the one or more optical signals may be emitted by the target site in absence of any exposure to an optical beam or other external illumination source. In an example, the target site may emit at least a portion of the electromagnetic spectrum, such as infrared radiation.

In some cases, the one or more optical signals reflected or emitted from the target site may comprise infrared light or infrared radiation. Infrared radiation emission by the target site may range from the red edge of the visible spectrum at a wavelength of about 700 nanometers (nm) to about 1 millimeter (mm), which is approximately equivalent to a frequency of about 430 terahertz (THz) to about 300 gigahertz (GHz). Regions within the infrared spectrum may include, for example, near-infrared (NIR), short-wavelength infrared (SWIR), mid-wavelength infrared (MWIR), intermediate infrared (IIR), long-wavelength infrared (LWIR), and far-infrared (FIR). Near-infrared signal may range from about 0.7 micrometer (m) to about 1.4 m, which is approximately equivalent to a frequency of about 214 THz to about 400 THz. Long-wavelength infrared may range from about 8 m to about 15 m, which is approximately equivalent to a frequency of about 20 THz to about 37 THz.

The distal end of the scope 105 may capture at least a portion of the one or more optical signals. The scope may transmit at least a portion of the one or more optical signals from the distal end of the scope 105 through the elongated body of the scope. As an example, the scope may transmit coherent laser light, from an illumination source, through the elongated body of the scope, to illuminate a target site. The target site may generate backscattered light upon exposure to the coherent laser light, and at least a portion of the backscattered light may enter back into the distal end of the scope 105. The scope may transmit at least a portion of the backscattered light through the elongated body of the scope towards an imaging unit and/or one or more imaging sensors. In another example, the scope may transmit white light from an illumination source out of the distal end of the scope, to illuminate a target site. The target site may generate reflected light upon exposure to the white light, and at least a portion of the reflected light may enter back into the distal end of the scope 105. The scope may transmit at least a portion of the backscattered light through the elongated body of the scope towards an imaging unit and/or one or more imaging sensors.

In some cases, the system may comprise one or more lenses. The one or more lenses may be positioned or located within one or more components of the system, or within the housing of the system as a whole. In some cases, the one or more lenses may be positioned or located within the scope. For example, the one or more lenses may be positioned or located within the elongated body of the scope (e.g., in a light channel formed by the body of the scope). The one or more lenses may be positioned or located in different components of the system e.g., the imaging module and/or the elongated body of the scope. The one or more lenses may be positioned or located adjacent to the distal end and/or the proximal end of the elongated body of the scope.

In some cases, the one or more lenses may be configured to adjust a field of view or an angle of view of the surgical scene. In some cases, the one or more lenses may comprise an optical aperture or an objective lens for focusing or adjusting a focus of light. The one or more lenses may be positioned in front of a beam splitter (e.g., before the light signals transmitted from the surgical scene reach the beam splitter).

In some cases, the scope may comprise one or more rod lenses within the elongated portion of the scope. In other cases, the scope may comprise one or more objective assemblies disposed within the elongated portion of the scope.

In some cases, the system may comprise a single assembly that is capable of rotating as a single device. Alternatively, the system may comprise multiple components or portions that may be rotatable independently of one another.

In some cases, the system may comprise a first portion or component and a second portion or component. The first portion or component and the second portion or component may comprise, for example, the scope, the body of the scope, one or more optics inside or within the body of the scope, the imaging module, one or more coupling mechanisms to couple the scope to the imaging module, the imaging unit, the imaging sensor, and/or the eyepiece of the system.

In some cases, a first portion or component of the imaging device may be rotatable relative to a second portion or component of the imaging device. In an example, the scope may be configured to rotate relative to the imaging module (see, e.g., FIGS. 3A-3D). In an example, the elongated portion of the housing is rotatable relative to the first imaging unit. In some cases, the first portion or component may rotate relative to the second portion or component without changing the field of view or angle of view of the surgical scene. In other cases, the first portion or component may rotate relative to the second portion or component to change the field of view or angle of view of the surgical scene. Such rotation may or may not change the position or orientation of the imaging unit, imaging sensor, the optical elements, and/or the eyepiece of the system.

In some cases, the scope may be configured to rotate relative to one or more of the imaging module, the imaging unit, the imaging sensor, or the eyepiece. In some cases, the scope may be rotatable relative to the imaging module and/or the imaging unit. In some cases, the rotation of the scope may be permitted by a coupling between the scope body and the imaging module.

FIGS. 3A-3D illustrate different embodiments of a scope 310 that may be held in a fixed position and/or orientation relative to an imaging module 320. In some cases, the distal end of the scope may be rotated relative to the imaging module 320. Such rotation may allow the distal scope optics to rotate relative to the body of the scope, thereby enhancing the field of view observable using an angled view scope. In some cases, a first portion of the system can rotate 340*a* in relation to a second portion of the system. (See FIG. 3B). In some cases, a first portion of the system may rotate 340*b* with respect to a second portion of the system. The system may comprise a bearing or any other rotatable coupling or component 330 between the body of the scope 310 and the imaging module 320. (See FIGS. 3A-C). In an example, the first portion of the system can be the scope 310 or the imaging module 320. In an example, the second portion of the system can be the imaging module 320 or the imaging unit 350. In an example, the rotation can occur either proximal or distal the rotatable coupling 330, or both. As shown in FIG. 3D, the imaging module 320 is releasably attachable to different scopes 310*a-d*. Examples of scopes 310*a-d* can include scopes with differing number of relay lenses. In some cases, the rotation allows for more natural visualization of the user while maintaining the optical pairing in place between the scope body and the imaging module or the imagine device and the imaging unit. In some case, scopes 310*a-d* can include different coupling adaptors on their proximal end to couple with the imaging module 320. In an example, a coupling adaptor can be objective adaptor 510, 610 described elsewhere or any other coupler.

In some cases, the imaging device may provide a field of view of the surgical scene. In some cases, the field of view may comprise one or more regions of the surgical scene that are viewable or detectable using the imaging sensor or the imaging unit, or both. The imaging device may provide an angle of view of the surgical scene. The field of view may provide a visualization of the surgical scene. The field of view may encompass the entire surgical scene or a portion thereof.

In some cases, the field of view of an image from the first imaging unit, the second imaging unit, or both can be configured to comprise a marker configured to aid in positioning or alignment the first imaging unit relative to the second imaging unit. For example, the marker can be any one or more of marker 710, 804, 1110, 1112, 1114. (See, e.g., FIG. 7, FIGS. 8A-8B, FIGS. 10A-10D, FIGS. 11A-11C). In an example, the marker can be an optical marker. In some cases, the field of view provided by the imaging device may comprise a marker to aid in positioning or alignment of the system relative to one or more features or regions of the surgical scene. In some cases, the marker may comprise a notch. In some cases, the notch can be used to determine a sharpness of the marker which may correlated with at least one of the calibration and alignment of the first imaging unit relative to the second imaging unit. (See, e.g., FIGS. 11A-11C). For example, in reference to FIG. 11A, notch in marker 1110 is shown having sharp edges while notch in marker 1112 is shown blurry, while notch in marker 1114 is shown entirely out of focus.

In some cases, the marker comprises a fiducial marker. In some cases, the marker can include one or more fiducial marks or pattern of graduated notches for aiding in dynamic calibration, aligning, blending, and overlaying of images and videos. For example, FIG. 10D shows a fiducial marker 1024 including a first set of fiducial marks 1024' and a second set of fiducial marks 1024". In some cases, the first set of fiducial marks 1024' can have more fine or narrow notches as compared to the second set of fiducial marks 1024". In some cases, the user can use the differences in resolution of the notches between the first set of fiducial marks 1024' and the second set of fiducial marks 1024" to determine an adjustment needed to come into focus. In some cases, the image processor can use this difference in fiducial marks to determine an adjustment needed to come into focus.

Figure 7:
FIG. 7 illustrates an image of a surgical scene imaged at an image sensor plane and provided to user, in accordance with some embodiments.

In some cases, the field of view provided by the imaging device may comprise a marker. The marker may comprise for example a 100×100 micron square obscuration placed at the x,y coordinates to obscure or block all light that is directed to the upper right hand edge of the field. This may produce for example a small square in the surgical image as shown in FIG. 7. The marker shape is not limited to rectangular markers and other shapes comprising circles, triangles, letters, lines may be used without deviation from the present invention. The marker may aid in positioning or alignment of the system. The alignment of the system may be relative to one or more features or regions of the surgical scene. In some cases, the field of view comprising a marker may allow the field of view to be configured or adjusted to match a previously recorded or annotated field of view of the same surgical scene, or a different surgical scene. In some cases, the marker can be projected on the surgical scene, displayed on a monitor, viewed through virtual or augmented reality, or projected on a lens of the scope. In some cases, the marker can be used to calibrate, align, blend, and overlay images and videos. In some cases, the notch or fiducial marker may aid a user or an image calibration unit in manually or automatically aligning the field of view or angle of view of the scope with one or more viewing angles of interest (e.g., standard or preferred surgical views or perspectives) or with respect to one or more features present within the surgical scene with greater precision than a marker alone.

Figure 8A:
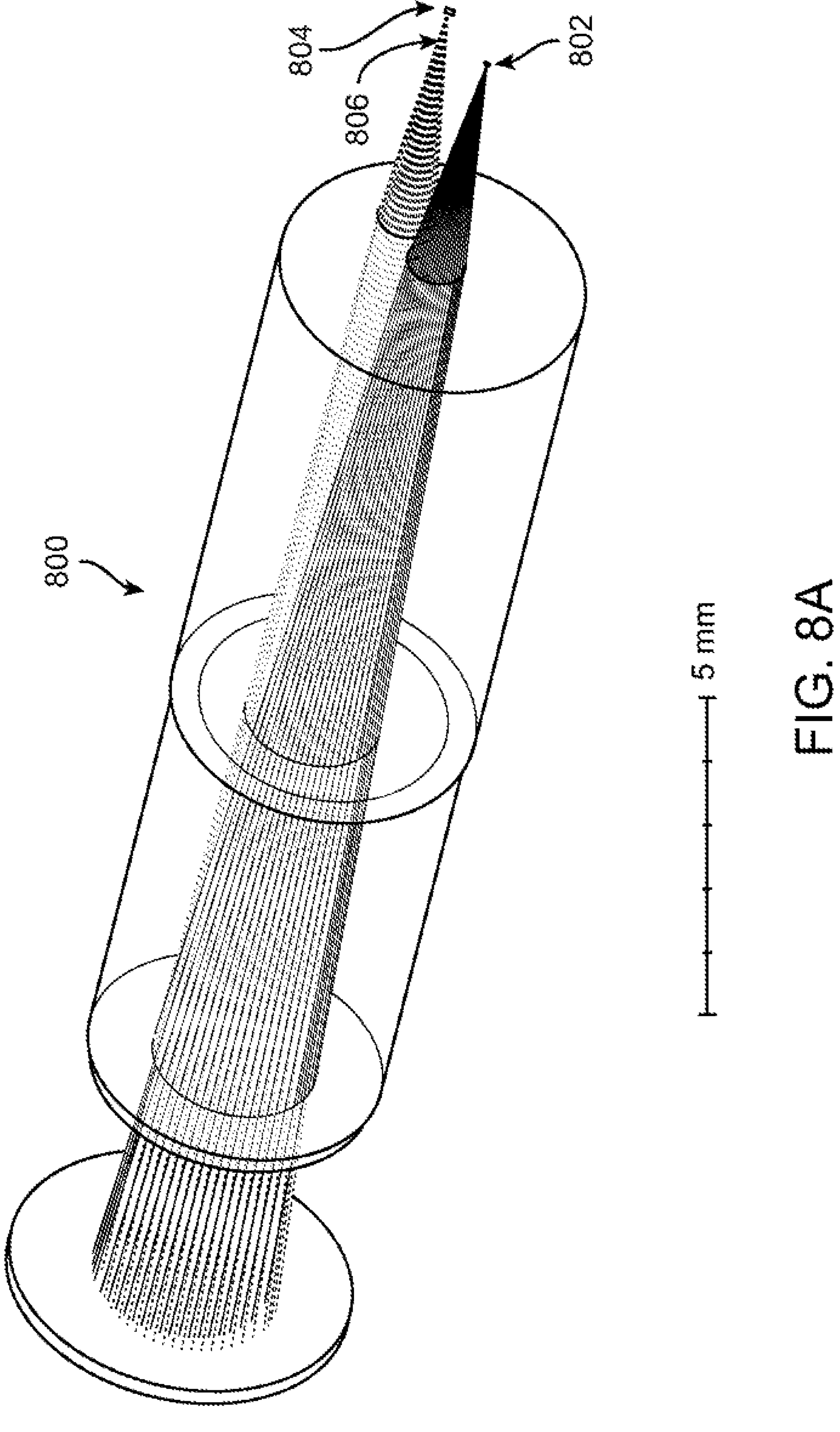
FIGS. 8A-8B illustrate a fiducial at intermediate focal point projecting from a relay lens, in accordance with some embodiments.
Figure 8B:
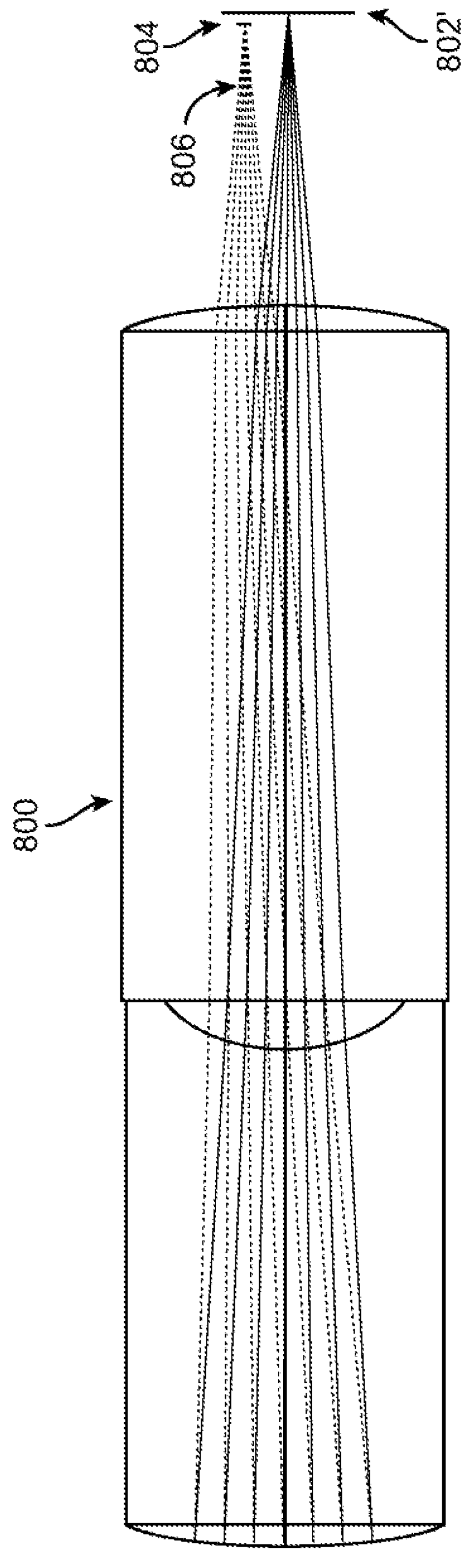
Figure 8B:
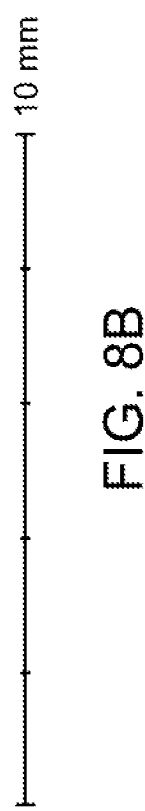

In some cases, the optical path comprises one or more obstructions between one or more pairs of lenses, and the one or more obstructions may appear in the field of view as the marker. In an example, an obstruction can be marker 804 as shown in FIGS. 8A and 8B.

In some cases, the imaging device comprises an optical source configured to project one or more visual references onto the surgical scene, where the one or more visual references may appear in the field of view as the marker. In an example, the optical path comprises one or more lenses for adjusting a field of view or an angle of view of the surgical scene. In an example, the optical path comprises one or more rod lenses or objective assemblies.

In some cases, the integrated scope system may comprise an imaging module 120, 220, 320 (see FIGS. 1B, FIG. 2, and FIGS. 3A-3C). The imaging module may comprise one or more imaging sensors and/or one or more optical elements as described elsewhere herein. In some cases, the imaging module may be (i) integrated with the scope and (ii) disposed between the proximal end of the scope and the distal end of the scope. Such integration may allow the scope and the imaging module to be provided and used as a single unit or instrument. Such integration may not or need not require any external fasteners or coupling mechanisms.

As used herein, integration may refer to the components of the present system being housed within the same apparatus, being permanently coupled together, or otherwise formed as and/or functioning as a single unit or device. The presently disclosed systems may comprise an integrated imaging system that includes an imaging module, one or more optical elements, and/or an image processor joined together with and/or physically or operably coupled to a scope to form a single unit or device.

In some cases, the integration of the system may prevent light and/or fluid from entering into or escaping from one or more of the components of the system. In some cases, the system may be integrated such that the spatial relationship (e.g., relative position or orientation) between two or more of the system components remain fixed or constant. In some cases, the integration may still permit an adjustment of the spatial relationship between two or more of the system components.

The housing may comprise one or more biologically acceptable and/or compatible materials suitable for medical applications, depending on the particular application and/or preference of a medical practitioner. For example, components of the housing may include or be fabricated from materials such as polyvinyl chloride, polyvinylidene chloride, low density polyethylene, linear low density polyethylene, polyisobutene, poly(ethylene-vinylacetate) copolymer, lightweight aluminum foil and combinations thereof, stainless steel alloys, commercially pure titanium, titanium alloys, silver alloys, copper alloys, Grade 5 titanium, superelastic titanium alloys, cobalt-chrome alloys, stainless steel alloys, superelastic metallic alloys (e.g., Nitinol or super elasto-plastic metals), ceramics and composites thereof such as calcium phosphate (e.g., SKELITE™ manufactured by Biologix Inc.), thermoplastics such as polyaryletherketone (PAEK) including polyetheretherketone (PEEK), polyetherketoneketone (PEKK) and polyetherketone (PEK), carbon-PEEK composites, PEEK-BaS04 polymeric rubbers, polyethylene terephthalate (PET), fabric, silicone, polyurethane, silicone-polyurethane copolymers, polymeric rubbers, polyolefin rubbers, hydrogels, semi-rigid and rigid materials, elastomers, rubbers, thermoplastic elastomers, thermoset elastomers, elastomeric composites, rigid polymers including polyphenylene, polyamide, polyimide, polyetherimide, polyethylene, epoxy, glass, and/or any combinations thereof.

In some cases, at least a portion of the housing may be opaque, semi-transparent, or transparent. In some cases, the housing may be opaque and configured to block any external light from (i) entering through the housing into one or more components within the housing and (ii) interfering with the one or more light signals from the target site of the subject that is received by the imaging module.

In some cases, the housing may be configured to house one or more optical elements for directing light from the surgical scene to the imaging unit and/or the imaging sensor. In some cases, the imaging module may further comprise one or more optical elements disposed within the housing. The one or more optical elements may comprise a mirror, such as a longpass dichroic mirror or shortpass dichroic mirror, one or more lenses, such as a rod lens, objective assembly, aperture or other lens, prism, and/or a beam splitter. The one or more optical elements may be configured to direct light signals to the imaging unit and/or the imaging sensor. In some cases, the imaging module may comprise a user interface 228 having one or more buttons. The one or more buttons may be configured to receive a physical input from a user. In some cases, the physical input may control or fine tune an operation of the imaging module, an image processor or the imaging unit. In an example, the physical input controls an operation of the first imaging unit, the second imaging unit, a processor coupled to the first imaging unit, the second imaging unit, or both, or any combination thereof. In some cases, the imaging module may allow a user (e.g., a medical practitioner such as a physician, nurse practitioner, nurse, imaging specialist, etc.) to visualize and/or analyze a target site of a subject, such as internal tissue of a patient, in one or more ways that any traditional scope assembly alone cannot. In some cases, the buttons on the user interface can be controlled using magnets. In some cases, the benefit of using magnets for controlling the user interface allows for harsher sterilization methods for the imaging device.

In some cases, the first imaging unit and the second imaging unit have different imaging modalities. In some cases, the first imaging unit, the second imaging unit, or both comprises at least one of an imaging sensor, camera, an infrared sensor, or a sensor for RGB imaging. In an example, the first optical signal can have a first range of wavelengths and the second optical signal can have a second range of wavelengths. In an example, the first optical signal is a laser speckle imaging signal and the second optical signal is an RGB imaging signal. In an example, the first optical signal is an RGB imaging signal, and the second optical signal is a laser speckle imaging signal. In an example, different imaging modalities comprise at least one imaging modality selected from the group consisting of an infrared imaging sensor for laser speckle imaging, a fluorescence imaging sensor for fluorescence imaging, and a mosaic sensor for hyperspectral imaging, a short wave infrared (SWIR) sensor for SWIR imaging, a depth sensor for depth imaging.

In some cases, imaging devices and systems of the present disclosure may comprise at least one sensor (e.g., an imaging sensor). In some cases, the at least one sensor may be housed within the housing of the imaging module. The imaging module may comprise at least one imaging sensor. The system may comprise at least 1, 2, 3, 4, 5, or more sensors. The system may comprise at most 5, 4, 3, 2, or 1 sensor. Examples of the one or more sensors may include, but are not limited to, pressure sensor, temperature sensor, optical sensor (e.g., image sensor), infrared sensor, fluorescence imaging sensor for fluorescence imaging, depth sensor for depth imaging, gas composition sensor, membrane or diaphragm sensor, thin film sensor, resistive or capacitive sensor, or other type of sensing device. In some cases, the at least one imaging sensor may comprise two or more imaging sensors. The two or more imaging sensors may have different imaging modalities. In some cases, the two or more imaging sensors may comprise any of the at least one sensors described herein, including but not limited to, one or more of an infrared imaging sensor for laser speckle imaging, a fluorescence imaging sensor for fluorescence imaging, a mosaic sensor for hyperspectral imaging, a short wave infrared (SWIR) sensor for SWIR imaging, and a depth sensor for depth imaging.

Any of the sensors described herein may be permanently coupled to the imaging module or, alternatively, releasably coupled to the imaging module. In an example, one or more imaging sensors may be configured to releasably couple to the housing of the imaging module. In another example, one or more imaging sensors may be configured to releasably couple to the scope (e.g., at or near the proximal end of the elongated body).

In some cases, the one or more sensors (e.g., the image sensor) may be configured to generate a first set of imaging data from a first portion of the optical signals (e.g., light signals), and the imaging unit (e.g., the camera) may be configured to generate a second set of imaging data from a second portion of the optical signals (e.g., light signals). The first set of imaging data and the second set of imaging data may be the same. In an example, the first and second set of imaging data may be the same in order to confirm validity of the collected data. Alternatively, the first and second set of imaging data may be different, e.g., may correspond to different features of the target site, or may be obtained using different imaging modalities. The first set of imaging data may complement the second set of imaging data. In an example, the image sensor of the imaging device may be used for laser speckle imaging. In such a case, the first set of imaging data may comprise one or more laser speckle patterns, and the second set of imaging data may comprise one or more photographic and/or video images. The first set of imaging data may comprise at least 1, 2, 3, 4, 5, 6, 7, 8, 9, 10, or more laser speckle patterns. The first set of imaging data may comprise at most 10, 9, 8, 7, 6, 5, 4, 3, 2, or 1 laser speckle pattern.

Examples of features of the target site that may be detected by the image sensor and recorded in the first set of imaging data may include, but are not limited to, temperature, surface depth (i.e., tomography), blood flow rate, blood flow direction, oxygen concentration (e.g., in the blood), calcium potential, electrical potential, magnetic field, presence of one or more markers of interest (e.g., immunological staining), etc.

Figure 5B:
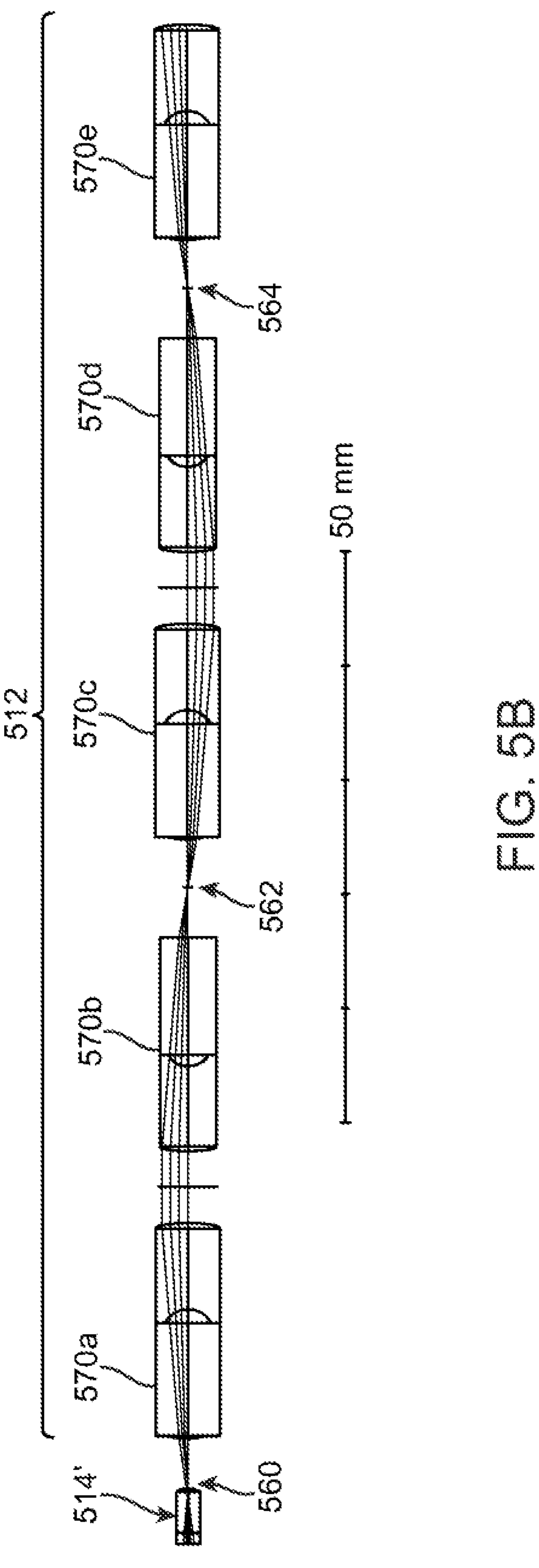
Figure 5C:
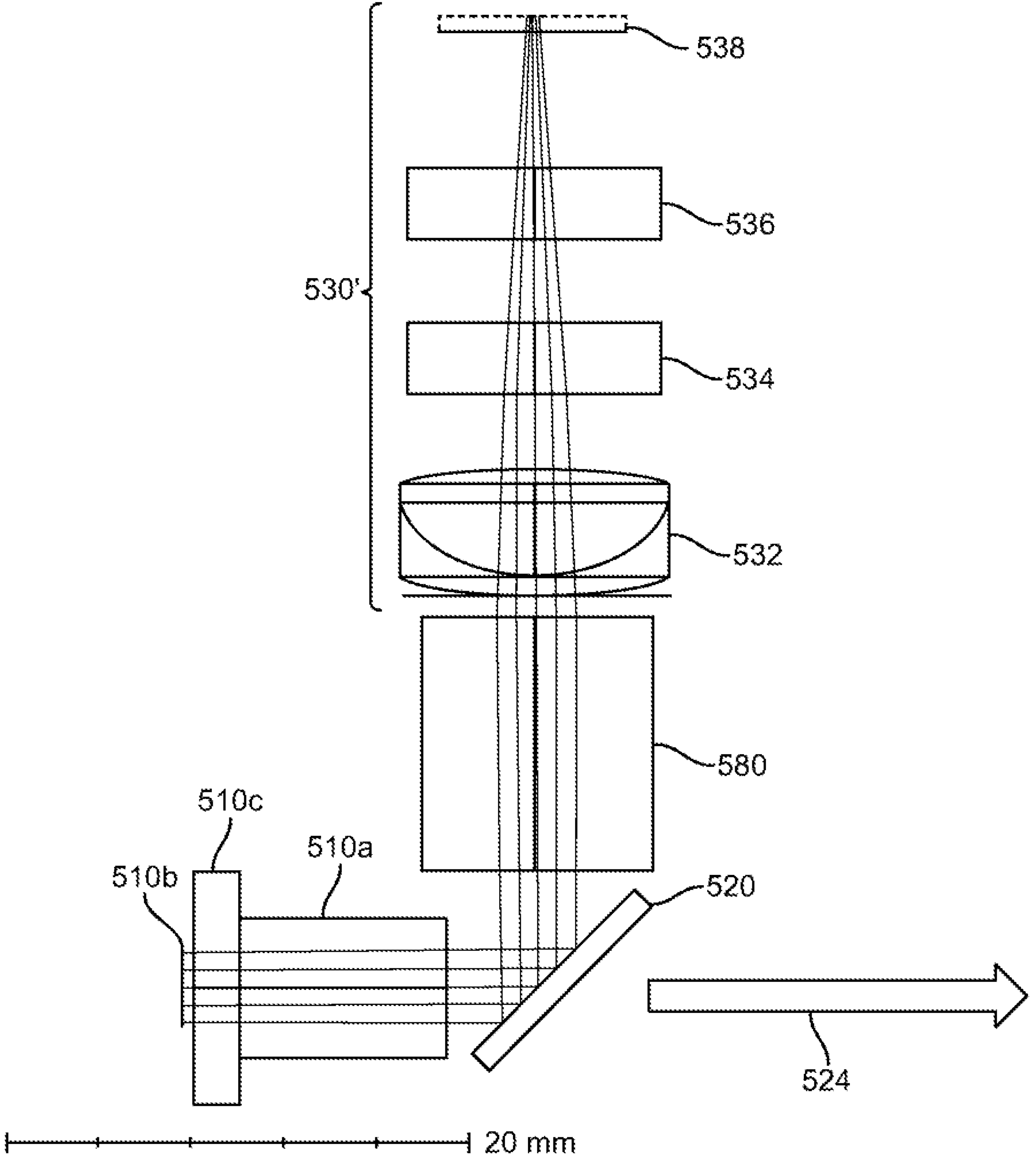
Figure 5D:
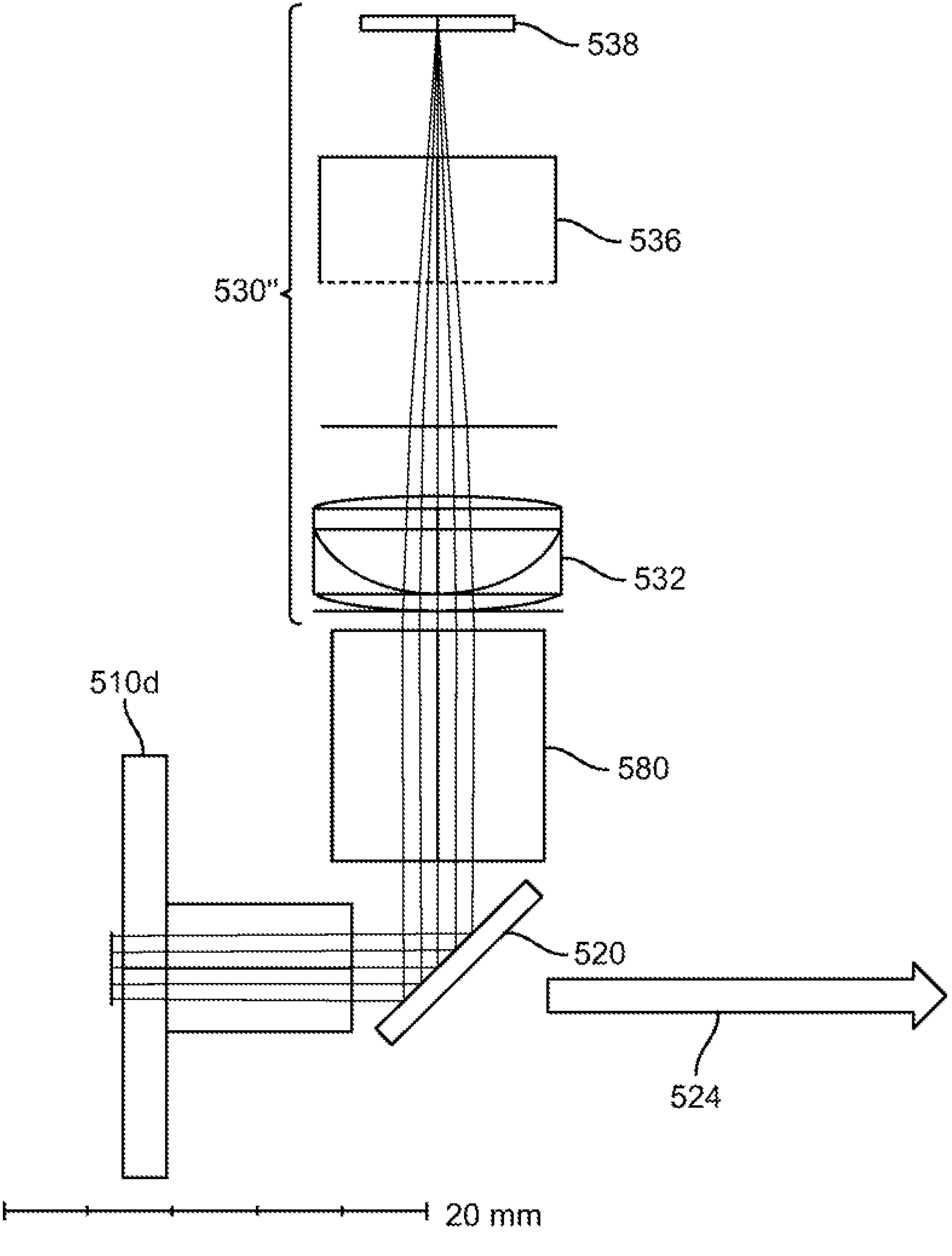
Figures 6A, 6B:
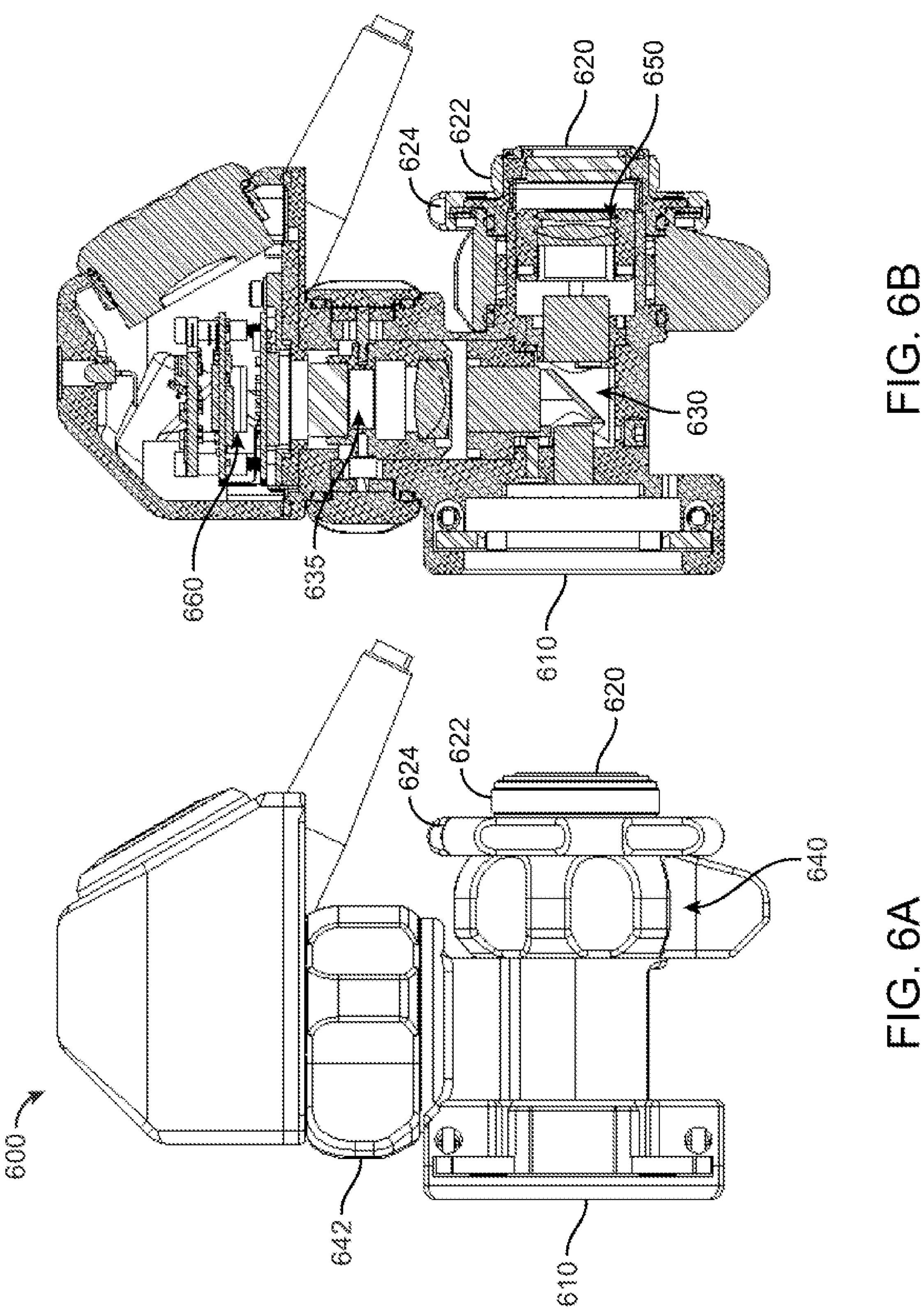
FIGS. 6A and 6B illustrate a cross-section of an imaging module, in accordance with some embodiments.

Turning to FIGS. 5A-5C, optical elements an integrated scope system 500 are shown directing optical signals 504 from a surgical scene 502. In an embodiment, optical elements may include an objective adaptor 510, 610 in communication with relay lenses 512 which are in communication with an objective lens group 514. The objective adaptor 510 is in communication with a dichroic beam splitter 520 which may be configured to direct a first portion of optical signals 522 from a surgical scene 502 to an imaging module 530 and a second portion of optical signals 524 to a pupil relay lens set 540 and an output window 542 at the proximal end of the imaging device 100. In some cases, the output window 542 can have a RGB pass filter to pass RGB light to imaging unit 550. In an example, imaging unit 550 includes a camera lens 552 and an RGB sensor 554. In some cases, the optical elements of the integrated scope system 500 are configured such that an image from the surgical scene is flipped as anticipated by the imaging unit 550. In some cases, the imaging unit 550 may digitally flip or mirror the image from the surgical scene to accommodate variations in the optical elements. In an example, an imaging module 530' can include one or more of an infrared camera lens 532, an RGB block filter 534, a notch block filter 536, an infrared sensor image plane 538, and a glass tunnel 580. In an example, the notch block filter 536 can be an indocyanine green (ICG) notch block filter. In an example, the glass tunnel 580 can serve to physically space optical components (e.g., beam splitter or dichroic mirror) to give more space for other optical components or user the focusing knob.

In some cases, the objective adaptor 510, 610 serves to align optics of the scope 210 and imaging module 220. In some cases, the objective adaptor 510, 610 serves as an input window from the scope 210 and imaging module 220 for light to pass. In some cases, the objective adaptor 510 can include attachment features 510*a-c* to secure the scope 210 and imaging module 220. In an example, the attachment features 510*a-c* can use a threaded connector, a spring, a magnet, a clip, a tongue and grove or any other suitable coupler. In some cases, the coupling mechanism includes optical components including a lens, a filter, a window, a prism, or any other optical element to aid in alignment of the optics of the scope 210 and imaging module 220.

In some cases, the optical elements may include one or more fiducials at one or more intermediate focal points. As shown in FIG. 5B, according to an example, the integrated scope system 500 can include a first fiducial 560 at a first intermediate focal point (x1, y1, z1) between a proximal end of the objective lens group 514' and lens 570*a*, a second fiducial 562 at a second intermediate focal point (−x2, −y2, z2) between lens 570*b* and lens 570*c*, and a third fiducial 564 at a third intermediate focal point (x1, y1, z3) between lens 570*d* and lens 570*e*.

Figure 9:
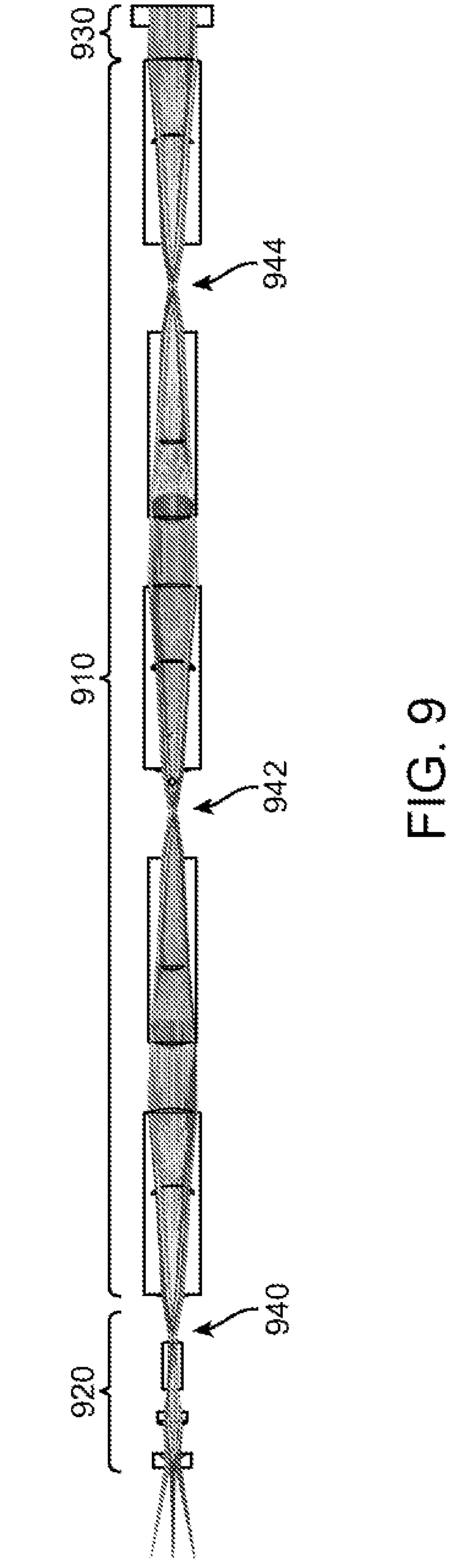
FIG. 9 illustrates an optical simulation showing light originating from three points and a set of fiducials at intermediate focal points within the optical elements of an integrated scope system, in accordance with some embodiments.

In some cases, a marker can project from a relay lens at intermediate focal point (see FIG. 8A and FIG. 8B). For example, FIG. 8A shows a marker 804 projecting from a relay lens 800 at intermediate focal point with a center image focal point at 802. In this example, the marker 804 is shown located in an upper right edge of field focal point 806. FIG. 8B shows an image plane 802' for 0D focus is shown for the center image focal point at 802 with the marker 804 projecting from the relay lens 800 at intermediate focal point in focus at −1D. In an example, the marker 804 in FIG. 8A forms an obscuration placed at the intermediate image at the 0D position blocking an optical ray bundle for the top right corner of the image, resulting in the image shown in FIG. 7. As the system is moved relative to an object, the plane of the intermediate image will move along the optical (z) axis. FIG. 9 illustrates an optical simulation showing light originating from three points on a distal end and a set of markers or fiducials at intermediate focal points within optical elements 900 of an integrated scope system, in accordance with some embodiments. In an example, the set of fiducials can include at least one of a first fiducial 940 at a first intermediate focal point (x1, y1, z1), a second fiducial 942 at a second intermediate focal point (−x2, −y2, z2), and a third fiducial 944 at a third intermediate focal point (x1, y1, z3). In an example, the optical elements 900 include relay lenses 910 which are in communication with an objective lens group 920, and objective adaptor 930.

Figure 10A:
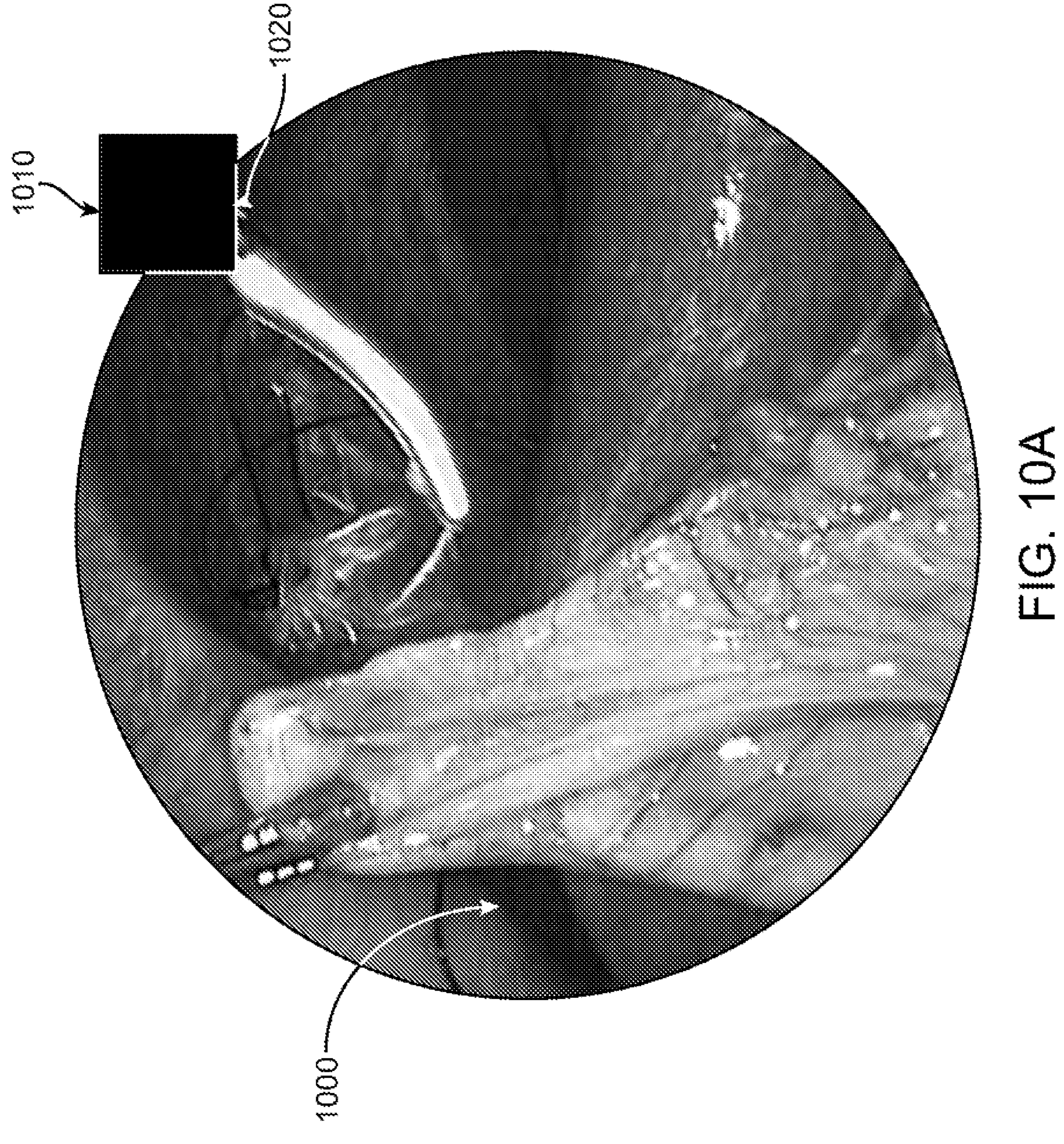
FIGS. 10A-D illustrate a surgical scene including a fiducial image at sensor image plane, showing an entire fiducial marker obscuration, where only a portion of the fiducial marker obscuration in the fiducial image will be visible by the user, in accordance with some embodiments.
Figure 10B:
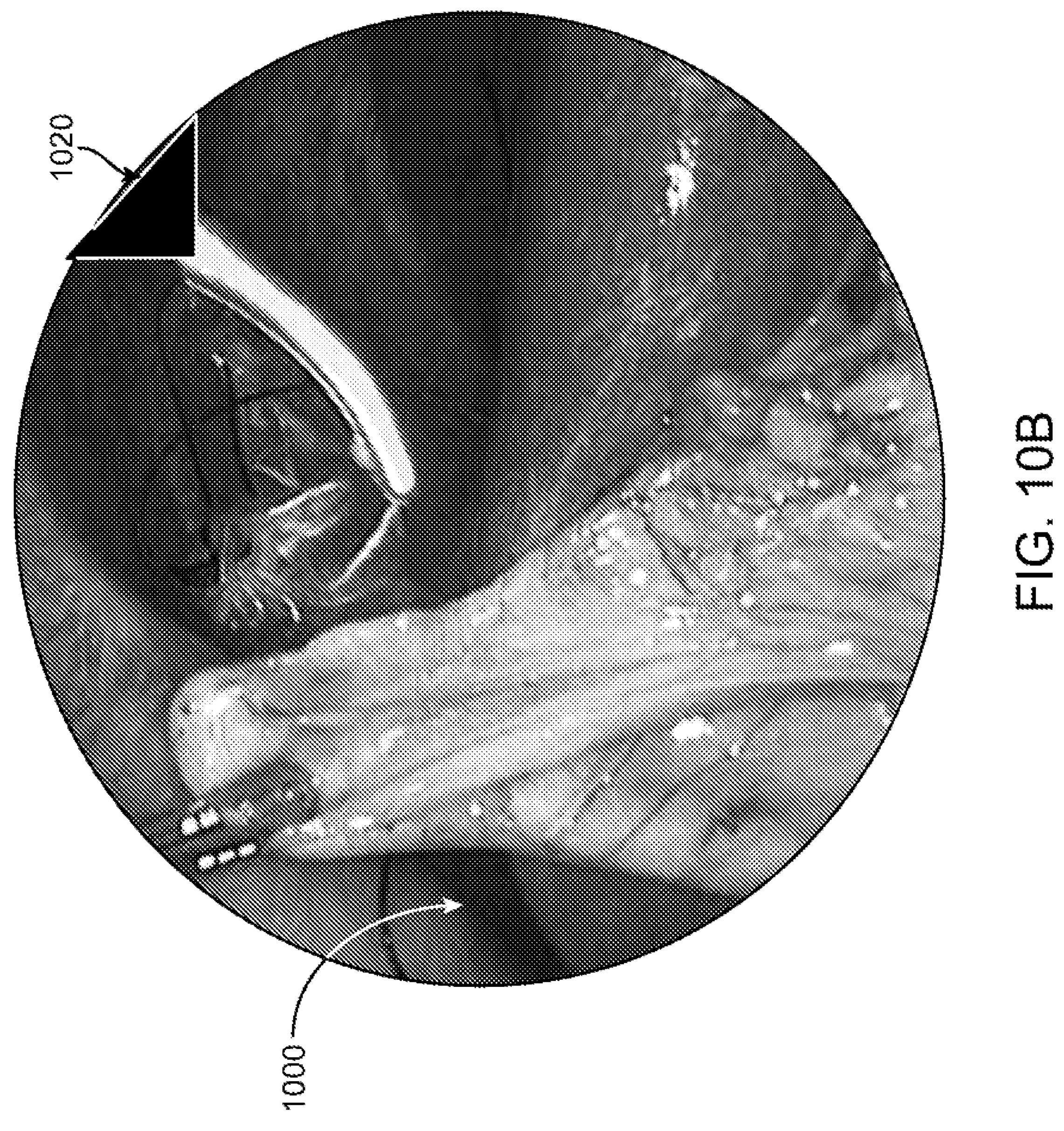
Figure 10C:
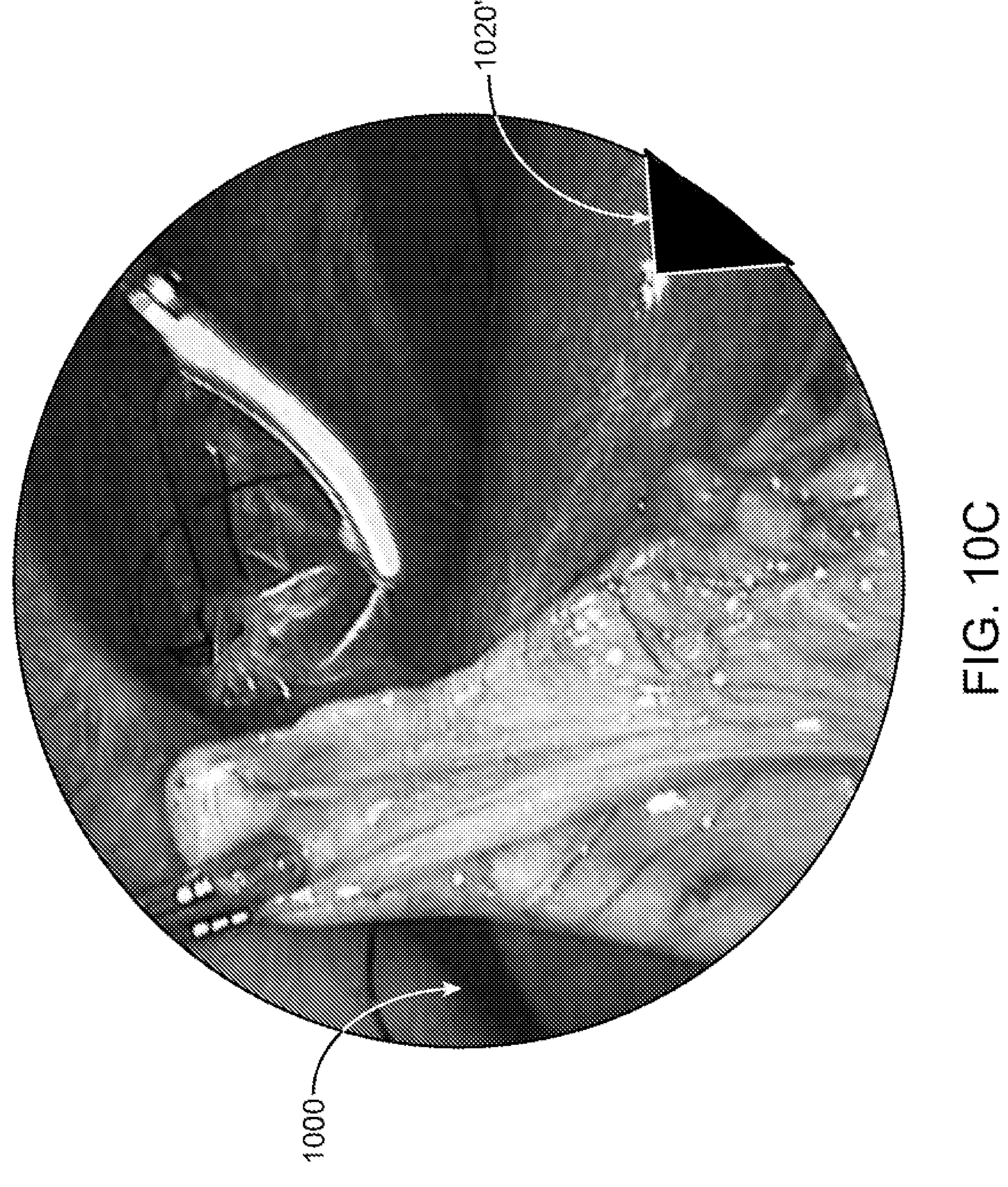
Figure 10D:
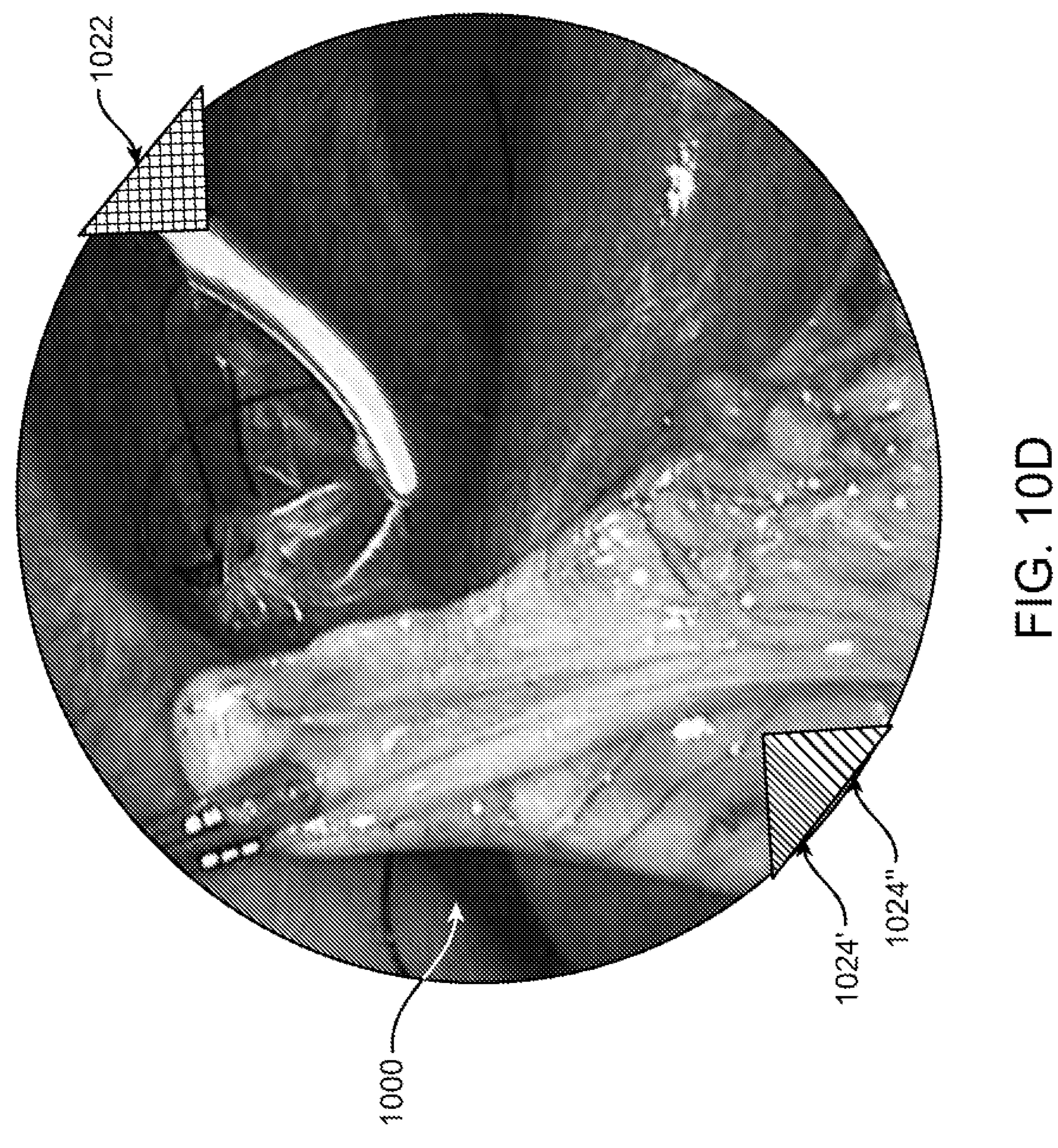

Turning to FIGS. 10A-10D, a surgical scene 1000 including a fiducial image at sensor image plane 1010 is shown illustrating an entire fiducial obscuration, where only a portion 1020 of the fiducial obscuration in the fiducial image will be visible by the user, in accordance with some embodiments. FIG. 10B shows only the portion 1020 of the fiducial obscuration in the fiducial image will be visible by the user. In an example, this can be a small blacked out marker which is ¼ the size of actual marker. In some cases, a field stop aperture may be used to define boundary of the fiducial image. In an example, the portion 1020' of the fiducial obscuration in the fiducial image at sensor image plane scope can be rotated +90 degrees (see FIG. 10C). This demonstrates how the fiducial follows rotation of the scope and/or imaging module and for a forward-looking scope the image does not rotate but the fiducial does. As shown in FIG. 10D, a first fiducial 1022 is located at the same x,y location instead of −x1, −y1 location for a second fiducial 1024. For this embodiment the fiducials are all located at the same x,y locations and therefore with the image inversion at the second fiducial, the second fiducial is located 180 degrees rotated from the first and third fiducials (1020, 1020'). This may be advantageous because the first fiducial 1022 will be in focus for 1 and 3 object distances at a first depth of focus and the second fiducial 1024 will be in focus for an object at a distance at a second depth of focus.

Figure 11A:
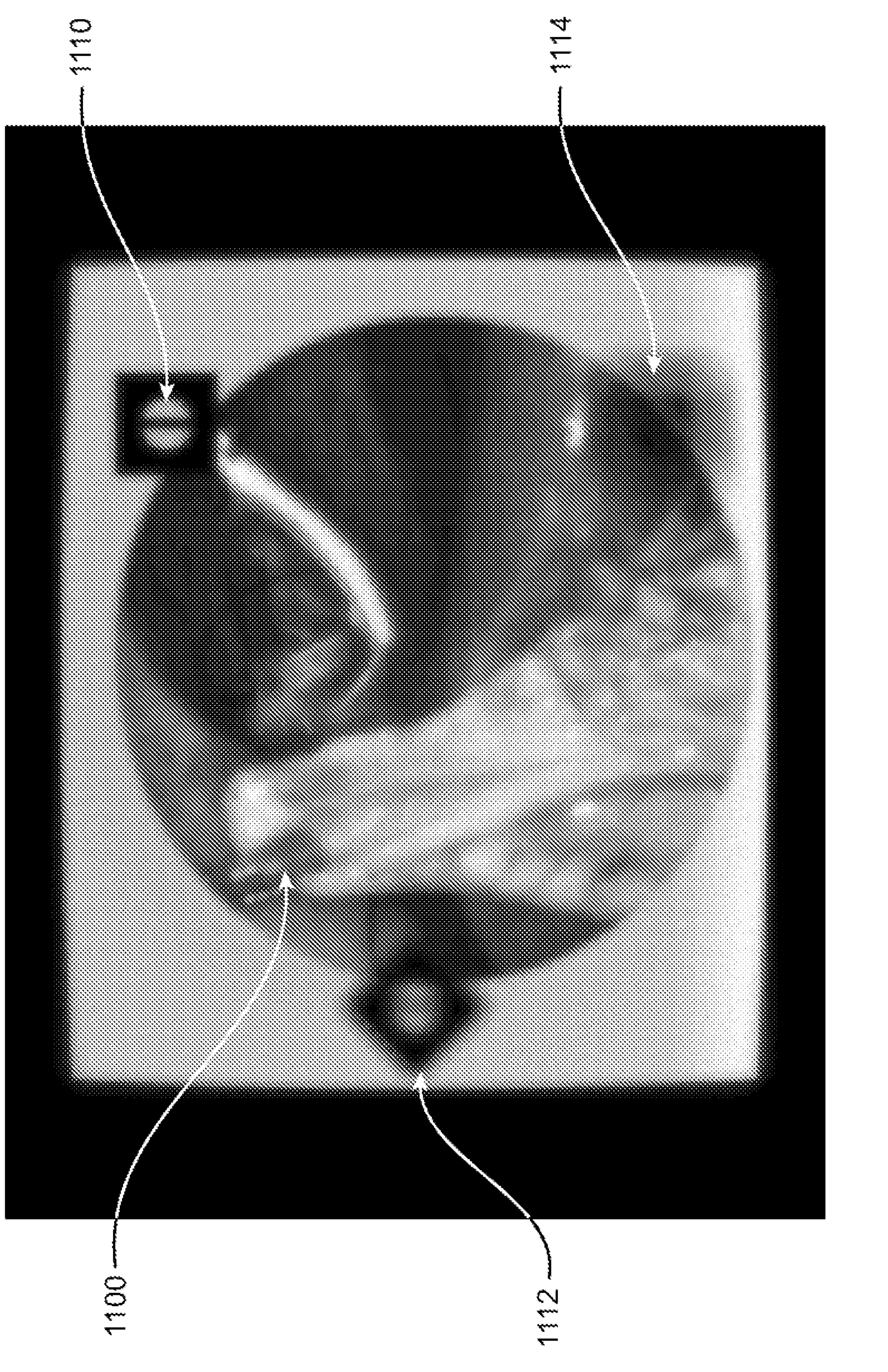
FIGS. 11A-11C illustrate images including fiducial markers with different features and locations indicating focus from an object distance with different fiducial markers in and out of focus, in accordance with some embodiments.
Figure 11B:
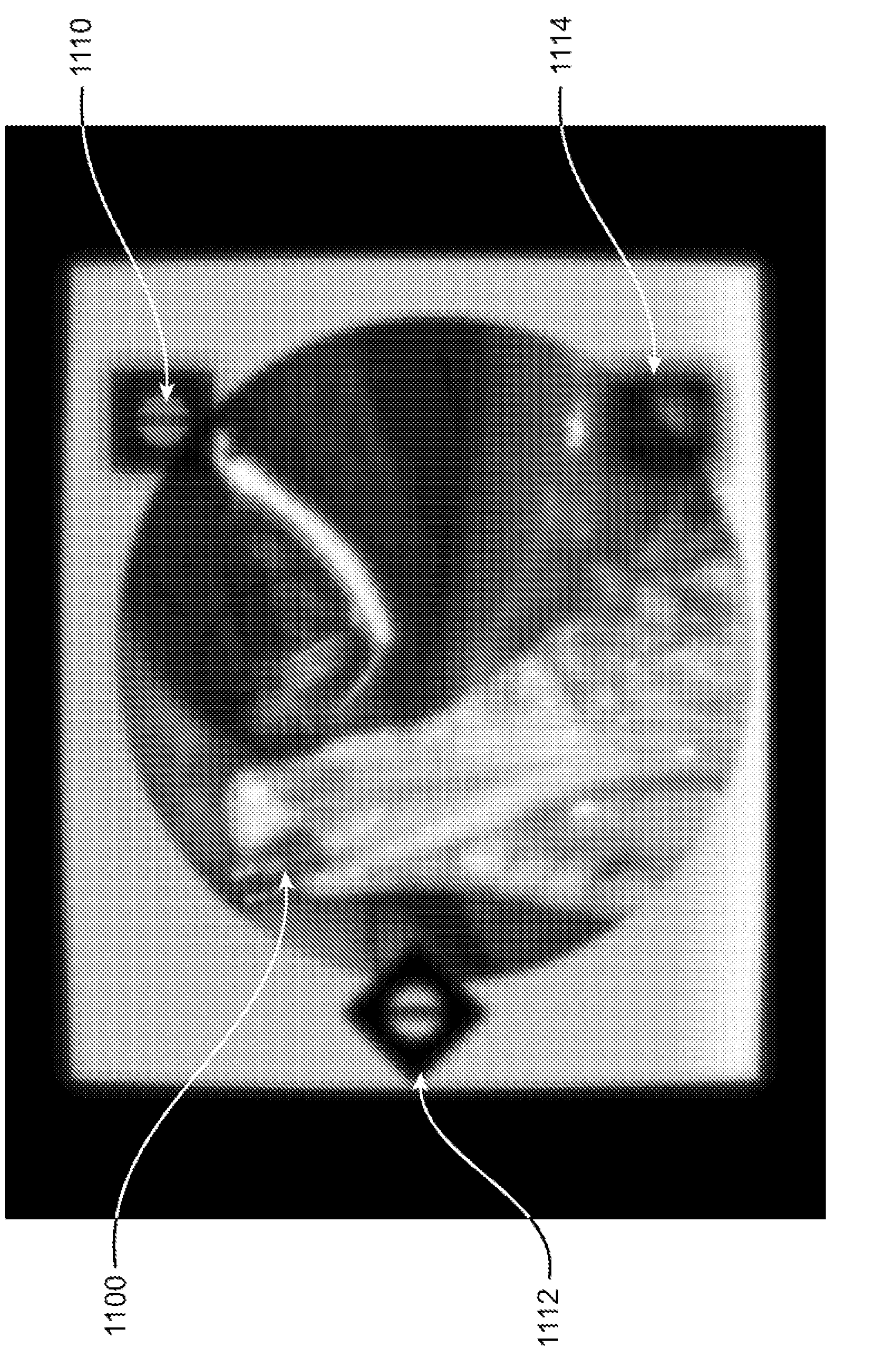
Figure 11C:
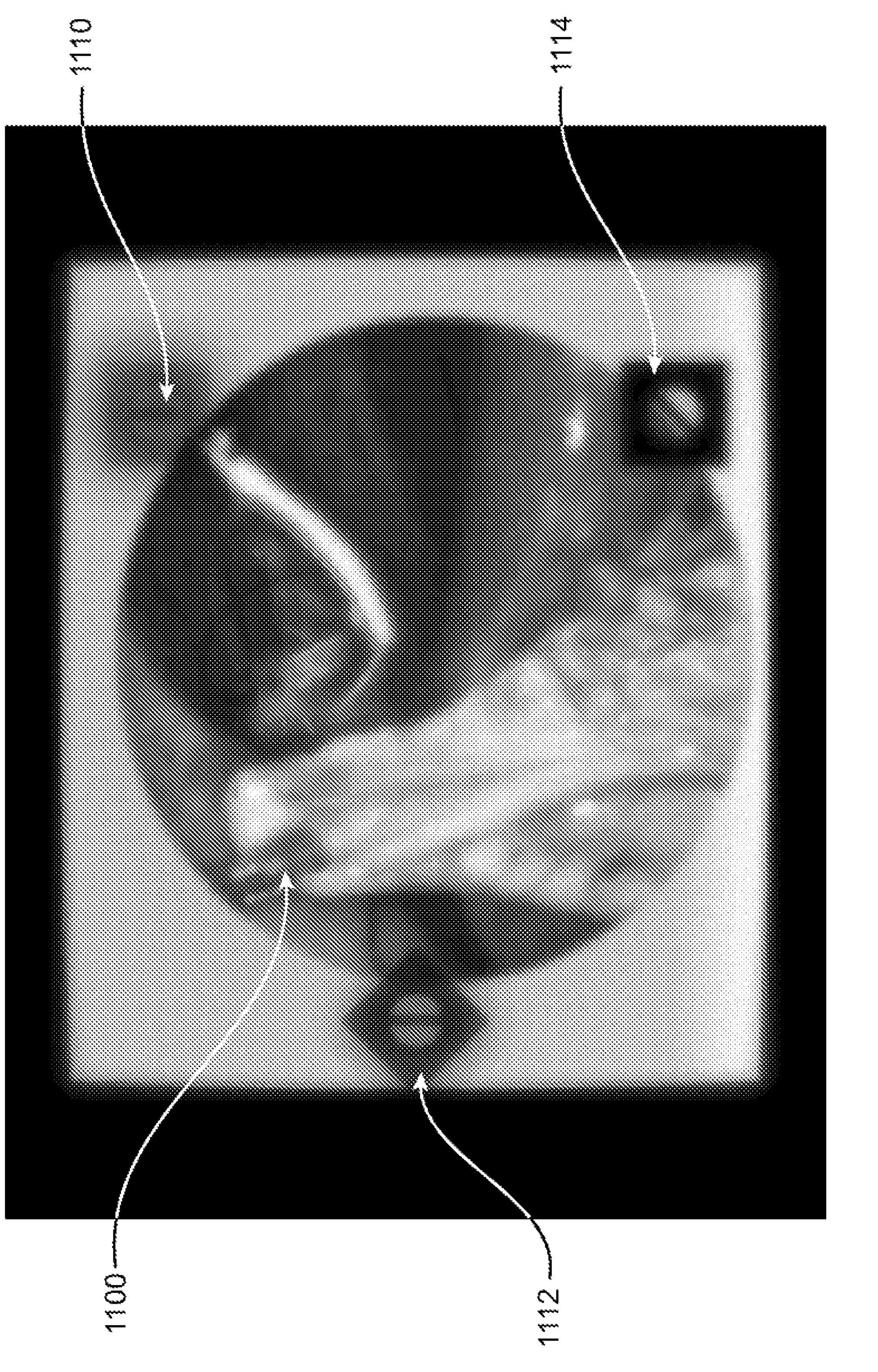

Turning to FIGS. 11A-11C, images are shown including fiducials with different features and locations indicating focus from an object distance with a different fiducials in and out of focus, in accordance with some embodiments. For example, FIG. 11A shows an image including fiducials with different features and locations indicating focus from Zemax geometrical ray trace object distance 10 mm, with a first fiducial 1110 in focus, a second fiducial 1112 out of focus, and a third fiducial 1114 out of focus. FIG. 11B shows an image including fiducials with different features and locations indicating focus from Zemax geometrical ray trace object distance 20 mm, with a first fiducial out of focus, a second fiducial in focus, and a third fiducial out of focus. FIG. 11C shows an image including fiducials with different features and locations indicating focus from Zemax geometrical ray trace object distance 10 mm with a first fiducial out of focus, a second fiducial out of focus, and a third fiducial in focus.

The imaging module may further comprise one or more optical elements. The one or more optical elements may be configured to receive light signals that are reflected from the target site and subsequently transmitted through the elongated body of the scope and (i) transmit the light signals to an imaging sensor or a camera, (ii) reflect the light signals in a predetermined direction (e.g., based on the wavelength of the light signals), (iii) focus the light signals, or (iv) otherwise modify a property of light signals or an optical path of at least a subset of the light signals.

In some cases, the one or more optical elements may comprise a mirror (e.g., a shortpass dichroic mirror or a long pass dichroic mirror), a prism, or a beam splitter. The one or more optical elements may be configured to direct one or more optical signals to or towards the at least one imaging sensor or the imaging unit. The one or more optical elements may be configured to direct one or more optical signals to the at least one imaging sensor of the imaging module. The one or more optical elements may be configured to direct one or more optical signals to the imaging unit. The one or more optical elements may be configured to direct one or more optical signals to the imaging module and one or more signals to the imaging unit. In an example, the one or more optical elements (e.g., a shortpass dichroic mirror) may be configured to reflect a first portion of the one or more optical signals onto the image sensor, while permitting a second portion of the one or more optical signals to pass through to the imaging unit. In another example, the one or more optical elements (e.g., a longpass dichroic mirror) may be configured to reflect a first portion of the light signals onto the imaging unit (e.g., a camera) while permitting a second portion of the light signals to pass through to the image sensor.

In some cases, the one or more optical elements may be configured to direct a first set of optical signals to the at least one sensor of the imaging module. The one or more optical elements may be configured to direct the first portion of optical signals to a first sensor of the two or more imaging sensors. The one or more optical elements may be configured to direct a second portion of optical signals to a second sensors of the two or more imaging sensors. The first portion of the optical signals may comprise deflected light (e.g., backscattered light) that is generated when the target site is illuminated with laser light (e.g., coherent laser light).

In some cases, the coherent laser light may be transmitted toward the target site via the scope (e.g., by one or more optical elements within the elongated body of the scope). The coherent laser light may be provided from a single laser source configured to emit a coherent laser light having a single wavelength. Non-limiting examples of the single laser source may include a single mode laser, a laser diode with a volume-holographic grating (VHG), or a laser with a laser clean-up filter (e.g., for narrow bandpass).

The coherent laser light may be provided from a plurality of laser sources having a plurality of different wavelengths. The plurality of different wavelengths may lie in an invisible spectrum. The invisible spectrum may comprise wavelengths (i) greater than about 700 nm and/or (ii) less than about 400 nm. In some cases, the invisible spectrum may comprise wavelengths (i) greater than about 770 nm and/or (ii) less than about 390 nm. The second portion of the light signals may comprise reflected light that is generated when the target site is illuminated with a different light (e.g., white light). In some cases, the different light may be a white light comprising a plurality of wavelengths in the visible spectrum, comprising wavelengths between about 400 nm to about 700 nm. In some cases, the white light may be transmitted toward the target site via the scope.

In some examples, the scope may comprise a plurality of optical paths to direct the coherent laser light and the white light separately from each other. In some examples, the scope may comprise a single optical path to direct a combined light that comprises both the coherent laser light and the white light.

In some cases, the one or more optical elements may comprise a beam splitter. The beam splitter may be configured to receive optical signals (e.g., light signals) from the target site and (i) reflect the first portion of the optical signals that is in a first electromagnetic spectral range toward the image sensor, and (ii) permit the second portion of the optical signals in a second electromagnetic spectral range to pass through toward the camera of the scope assembly. Alternatively, the beam splitter may be configured to receive optical signals from the target site and (i) reflect the second portion of the optical signals that is in the second electromagnetic spectral range toward the imaging unit, and (ii) permit the first portion of the light signals in the first electromagnetic spectral range to pass through toward a sensor of the one or more sensors in the imaging module. Examples of the beam splitter may include, but are not limited to, a half mirror, a dichroic beam splitter (e.g., a shortpass or longpass dichroic mirror), or a multi-band beam splitter. In an example, the beam splitter may be a cube comprising two prisms (e.g., two triangular glass prisms) disposed adjacent to each other.

In some cases, the first set of optical signals may have a first range of wavelengths. The second set of light signals may have a second range of wavelengths. In some cases, the first range of wavelengths may be greater than a threshold wavelength. The second range of wavelengths may be less than the threshold wavelength.

In some cases, the threshold wavelength may be about 500 nm to about 1,500 nm. In some cases, the threshold wavelength may be about 500 nm to about 600 nm, about 500 nm to about 700 nm, about 500 nm to about 800 nm, about 500 nm to about 900 nm, about 500 nm to about 1,200 nm, about 500 nm to about 1,500 nm, about 600 nm to about 700 nm, about 600 nm to about 800 nm, about 600 nm to about 900 nm, about 600 nm to about 1,200 nm, about 600 nm to about 1,500 nm, about 700 nm to about 800 nm, about 700 nm to about 900 nm, about 700 nm to about 1,200 nm, about 700 nm to about 1,500 nm, about 800 nm to about 900 nm, about 800 nm to about 1,200 nm, about 800 nm to about 1,500 nm, about 900 nm to about 1,200 nm, about 900 nm to about 1,500 nm, or about 1,200 nm to about 1,500 nm. In some cases, the threshold wavelength may be about 500 nm, about 600 nm, about 700 nm, about 800 nm, about 900 nm, about 1,200 nm, or about 1,500 nm. In some cases, the threshold wavelength may be at least about 500 nm, about 600 nm, about 700 nm, about 800 nm, about 900 nm, or about 1,200 nm. In some cases, the threshold wavelength may be at most about 600 nm, about 700 nm, about 800 nm, about 900 nm, about 1,200 nm, or about 1,500 nm. In an example, the threshold wavelength may be between about 700 nm to about 800 nm.

In some cases, the first set of light signals (with a wavelength greater than the threshold wavelength) may be usable for laser speckle imaging. The second set of light signals (having a wavelength lower than the threshold wavelength) may be usable for RGB imaging.

The imaging systems described herein may not or need not comprise any focusing device such as an objective lens or optical aperture. Alternatively, the imaging systems of the present disclosure may comprise one or more focusing devices. The imaging module may comprise at least 1, 2, 3, 4, 5, or more focusing devices.

A focusing device, as used herein in the present disclosure, may comprise any lens (e.g., fish-eye, elliptical, conical, etc.), reflector, optic, concentrator, or other device that is capable of reflecting, transmitting, or focusing light. In an example, the focusing device may be a relay lens.

The imaging module may comprise at least one focusing device (e.g., at least 1, 2, 3, 4, 5, or more focusing devices) for the image sensor 660. The at least one focusing device 635 may be disposed between the beam splitter 630 and the image sensor 660. The imaging module may comprise at least one focusing device (e.g., at least 1, 2, 3, 4, 5, or more focusing devices) for the camera. The at least one focusing device may be disposed between the beam splitter and the camera. In some cases, the imaging module may comprise at least one focusing device (e.g., at least 1, 2, 3, 4, 5, or more focusing devices) disposed in the optical path between the scope and the beam splitter.

In some cases, the one or more optical elements may comprise (i) a first focusing device 642 for the image sensor and (ii) a second focusing device 640 for the imaging unit. (See FIGS. 6A-6B). The first focusing device may be operatively coupled to a first focusing knob to adjust degree of focusing of the first focusing device. The first focusing knob may be operatively coupled (e.g., electronically or mechanically coupled) to the first focusing device. In an example, the first focusing knob may be mechanically coupled to the first focusing device via a first gearing mechanism comprising one or more gears. The first focusing knob may be operable by the user to adjust focusing of the first focusing device. The second focusing device may be operatively coupled to a second focusing knob to adjust degree of focusing of the second focusing device. The second focusing knob may be operatively coupled (e.g., electronically or mechanically coupled) to the second focusing device. In an example, the second focusing knob may be mechanically coupled to the second focusing device via a second gearing mechanism comprising one or more gears. The second focusing knob may be operable by the user to adjust focusing of the second focusing device.

In some cases, the first focusing device and the second focusing device may be operably coupled to each other (e.g., electronically or mechanically), such that focusing for the image sensor and for the camera can be performed concurrently. In an example, first and second focusing devices may be coupled to each other via a gearing mechanism comprising one or more gears. The first and second focusing devices may be coupled to a common focusing knob that is operable by the user. Alternatively, the first focusing device may be operatively coupled to a first focusing knob, the second focusing device may be operatively coupled to a second focusing knob, and the first and second focusing knobs may be operatively coupled to each other. In such case, (i) operating the first focusing knob may adjust degree of focusing of both the first and second focusing devices, and (ii) operating the second focusing knob may adjust degree of focusing of both the first and second focusing devices.

In some cases, any of the imaging devices described herein can comprise a housing, an insertion portion of housing, the insertion portion having an elongated optical axis, where a first optical signal and a second optical signal are transmitted along the elongated optical axis, where the first optical signal and the second optical signal each comprise a distinct wavelength range, and a beam splitter configured to deliver the first optical signal to the first imaging unit and configured to deliver the second optical signal to a second imaging unit, one or more markers along the elongated optical axis.

In some cases, any of the imaging devices described herein can comprise a focusing knob coupled to a lens on an optical path of either of the first imaging unit or the second imaging unit, where adjustment of the focusing knob is configured to bring an image of the one or more markers into focus on both of the first imaging unit and the second imaging unit.

In some cases, the first focusing device and the second focusing device may not or need not be operably coupled to each other. The first focusing device and the second focusing device may be provided separately and configured to be used independently of each other.

The at least one focusing device may be manually adjusted for focusing. In some cases, one or both of the first focusing device and the second focusing device may be manually adjusted for focusing. Alternatively, the at least one focusing device may be automatically adjusted for focusing. In some cases, the imaging module may be capable of autofocusing the at least one focusing device. In some cases, one or both of the first focusing device and the second focusing device may be automatically adjusted for focusing. In an example, focusing the first focusing device (e.g., manually or automatically) may consequently autofocus the second focusing device, or vice versa. In another example, the first and second focusing devices may be autofocused simultaneously.

In some cases, the imaging module may comprise at least one focusing device for the image sensor and no focusing device for the camera. In such cases, the camera may have its own focusing device. The at least one focusing device of the imaging module and the focusing device of the camera may or may not be operatively coupled to each other.

In some cases, the constant length of the scope may allow for a constant focal length for the optical signals transmitted to the image sensor or imaging unit (e.g., camera). In these cases, the system may not or need not comprise a focusing knob for the imaging unit or the imaging sensor.

In some cases, the systems described herein comprise an imaging device comprising a distal end for providing a field of view of a surgical scene and a proximal end that is releasably attachable to an external imaging unit, where the imaging device comprises an internal imaging unit that is (i) integrated with the scope and (ii) disposed between the proximal end of the scope and the distal end of the scope, where the external imaging unit comprises at least one imaging sensor and one or more optical elements for directing a first optical signal to the internal imaging unit and a second optical signal to the external imaging unit to which the imaging device is releasably attached.

In some cases, the imaging device may be releasably coupled to an imaging unit. The imaging unit may be releasably coupled to a proximal end of the imaging device. The imaging unit may comprise, for example, a camera or one or more imaging sensors. The imaging unit may comprise any camera or imaging sensor that is usable to obtain images of a surgical scene through an integrated scope system.

The imaging unit may be configured to transmit image signals or image data of the surgical scene to an imaging processor. The imaging unit may be configured to transmit image signals or image data of the surgical scene to the imaging processor in real-time. The image signals or image data transmitted to the imaging processor by the imaging unit may comprise RBG image data, infrared image data, fluorescence image data, and/or time of flight image data associated with the surgical scene. In an example, a user may change modes to visualize either laser speckle imaging or fluorescence imaging using the imaging processor.

The imaging unit and the scope may be operatively coupled together, e.g., mechanically or magnetically. The imaging device and imaging unit may be releasably coupled together. The imaging unit may be releasably attached to the proximal end of the imaging device (e.g., using one or more coupling mechanisms). The one or more coupling mechanisms may comprise, for example, magnets (e.g., electromagnets or permanent magnets), mechanical tethers (e.g., strings, threads, straps), adhesives (e.g., solids, semi-solids, gels, viscous liquids, etc.), male-to-female fasteners (e.g., mating or interlocking fasteners, hooks and holes, hooks and loops such as Velcro™, a female nut threaded onto a male bolt, a male protrusion inserted into a female indentation, screw-on couplings, and/or elastic couplings. In some cases, the coupling between the imaging unit and the imaging device may be reversible or irreversible. In some examples, the coupling may be a releasable coupling.

In some cases, the imaging unit may be configured to releasably couple to and decouple from the imaging device using a quick release mechanism (e.g., snap-fit, latches, etc.). The quick release mechanism may be configured to quickly move between a lock position (i.e., a coupled position) and a release position (i.e., a non-coupled position) in response to one or more movements of the quick release mechanism, such as a single, non-repetitious movement (e.g., lateral or rotational) of the quick release mechanism. The quick release mechanism may be configured to quickly move between a lock and a release position in response to a user instruction via a switch, e.g., a mechanical switch disposed on the imaging device.

The quick release mechanism may be configured to permit the user to releasably couple the proximal end of the imaging device to an imaging unit without use of tools. Alternatively, the quick release mechanism may be configured to permit the user to releasably couple the proximal end of the imaging device to an imaging unit with one or more tools, e.g., one or more keys to operatively coupled to the quick release mechanism to activate release of the quick release mechanism. The quick release mechanism may be configured to permit the user to releasably couple the proximal end of the imaging device to an imaging unit in less than 60 seconds. The quick release mechanism may be configured to permit the user to releasably couple the proximal end of the imaging device to an imaging unit in less than 60 seconds, 55 seconds, 50 seconds, 45 seconds, 40 seconds, 35 seconds, 30 seconds, 25 seconds, 20 seconds, 15 seconds, 10 seconds, 5 seconds, or less.

In some cases, the coupling between the proximal end of the imaging device and an imaging unit may not or need not utilize a quick release mechanism. In some cases, the imaging device may be screwed on to the imaging unit, thereby preventing a quick release of the imaging device from the proximal end of the scope. In an example, a coupling surface of the proximal end of the scope may substantially mimic the structure of a coupling surface of the camera, where the coupling surface of the camera is originally configured to couple to the imaging device.

The quick release mechanism may allow for precise coupling of two members, such as the proximal end of the imaging device and an imaging unit. The precise coupling may provide an optimal optical path between the two members. The precise coupling may be achieved within an accuracy of less than about 20 μm. In some cases, the precise coupling may be achieved within an accuracy of at most about 100 μm, 90 μm, 80 μm, 70 μm, 60 μm, 50 μm, 40 μm, 30 μm, 20 μm, 10 μm, 9 μm, 8 μm, 7 μm, 6 μm, 5 μm, μm, 3 μm, 2 μm, 1 μm, 900 nm, 800 nm, 700 nm, 600 nm, 500 nm, 400 nm, 300 nm, 200 nm, 100 nm, 50 nm, or less.

The imaging unit may be configured to releasably couple to scopes of various sizes. In the alternative, or in addition, the imaging device may be configured to releasably couple to the imaging unit using a quick release mechanism. The imaging device may also be configured to releasably couple to one or more imaging units of various sizes. In an example, the proximal end of the imaging device may comprise different sections with varied dimensions (e.g., different radial dimensions) configured to releasably couple to different imaging units having different sizes. In another example, the proximal end of the imaging device may comprise an adjustable mechanism to adjust a size, shape, profile, or diameter of the scope body to accommodate different imaging units having different sizes.

In some cases, the system may further comprise a processor such as an image processor operatively coupled to the at least one sensor and the imaging unit. In an example, the image processor can be a processor 405 described in relation to FIG. 4. The image processor may be configured to process one or more images obtained using the at least one sensor and/or the imaging unit to generate a visualization of the surgical scene. (See FIG. 7, FIGS. 10A-10D, FIGS. 11A-11C). In some cases, the visualization of the surgical scene comprises a dynamic overlay of images. In some cases, the dynamic overlay of images comprises a laser speckle image, a depth image, a fluorescence image, and/or an RGB image of the surgical scene. In some cases, the dynamic overlay of images is adjustable based on a user input or selection of a desired imaging modality. In an example, dynamic overlay of images is adjustable based on a user input or selection of a desired imaging modality.

In some cases, the processor may be operatively linked to the at least one sensor of the imaging module and the imaging unit. The image processor may be operatively coupled to the imaging unit and the imaging sensor of the imaging module. In some cases, the image processor can be operatively coupled to the first imaging unit, the second imaging unit, or both. In an example, the image processor is configured to process one or more images obtained using the first imaging unit, the second imaging unit, or both. In an example, the one or more images comprise one or more images of a surgical scene, and the image processor is configured to produce a visualization of a surgical scene. In an example, visualization of the surgical scene comprises a dynamic overlay of images. In an example, the dynamic overlay of images comprises one or more imaging modalities, the one or more imaging modalities selected from the group consisting of: a laser speckle image, a depth image, a fluorescence image, and an RGB image of the surgical scene.

The processor may be configured to direct the image sensor of the imaging module to capture a first set of imaging data and direct the imaging unit to capture a second set of imaging data. The processor may be further configured to generate one or more images of the surgical scene based on at least one of the first set of imaging data and the second set of imaging data.

In some cases, the image processor may be configured to generate one or more medical images. The one or more medical images may be obtained using the at least one sensor. The one or more medical images may be obtained using the imaging unit. The one or more medical images may be obtained using the at least one sensor and the imaging unit. The image processor may be configured to generate a visualization of the surgical scene using the one or more medical images.

The visualization of the surgical scene may allow a user (e.g., a medical practitioner such as a physician, nurse practitioner, nurse, imaging specialist, etc.) to understand multiple features (e.g., characteristics, aspects, etc.) of the target site at once. The visualization of the surgical scene may comprise one or more images. The visualization of the surgical scene may be dynamic. As used herein "dynamic" may refer to the ability of the visualization to change, adapt, be modified, or be updated to a more current version of the visualization or a different type of visualization (including, for example, a different type of imaging modality). The visualization of the surgical scene may comprise a dynamic overlay of two or more images. The dynamic overlay of images may be adjustable. The dynamic overlay of images may be adjusted by a user input or selection. The user input or selection may comprise a desired imaging modality.

Examples of features of the target site may include, but are not limited to, temperature, perfusion, surface depth (i.e., tomography), blood flow rate, oxygen concentration (e.g., in the blood), calcium potential, electrical potential, magnetic field, presence of one or more markers of interest (e.g., immunological staining), etc. The term "perfusion," as used herein, generally refers to passage of fluid through the circulatory system or lymphatic system to an organ or a tissue. In an example, perfusion may refer to the delivery of blood at the level of the arteries or capillaries, in which exchange of oxygen and/or nutrients between blood and tissue takes place. In some cases, perfusion may comprise flow rate of the fluid, volume of the fluid that is present or traversing across a target tissue site, a pattern of flow channels of the fluid at the target tissue site, or a combination thereof. In some cases, perfusion of the liquid of interest may be increasing, decreasing, or remaining substantially the same during one or more imaging processes. In some cases, any change in flow rate or volume of the perfusing fluid may be indicative of (i) one or more biological events or (ii) one or more surgical events occurring upstream of, downstream of, or substantially at the target tissue site. When quantified, perfusion may be measured as the rate at which blood is delivered to tissue, or volume of blood per unit time (blood flow) per unit tissue mass, in units of cubic meter per second per kilogram ($m^3/s/kg$) or milliliters per minute per grams (mL/min/g). A degree of perfusion may be indicative of one or more health conditions, e.g., cardiovascular disease such as coronary artery disease, cerebrovascular disease, peripheral artery disease, etc.

In some cases, the processor may be further configured to spatially (and/or temporally) align the first set and the second set of imaging data. In an example, the processor may perform digital image processing on one or both of the first set and the second set of imaging data (e.g., affine transformation of one or more pixels of the first set and the second set of imaging data), such that the perspectives of the image sensor and the camera are aligned (or lined up) and spatially correspond to each other. Such alignment of the imaging devices (imaging module, imaging unit) may be useful when creating an overlay of the first set and the second set of imaging data, e.g., when generating an overlay of blood flow and perfusion (e.g., from the image sensor) on top of the standard white light surgical view (e.g., from the camera). In other examples, the processor may be configured to perform image registration. The processor may be configured to find one or more matching features in the first set and the second set of imaging data, then calculate a transformation of one or both of the first set and the second set of imaging data for their alignment. Non-limiting examples of such features include corners, lines, speeded up robust features (SURF), and scale-invariant feature transformation (SIFT) features.

In some cases, the processor may be configured to compare the first set of imaging data and the second set of imaging data. Based at least in part on the comparison of the first and second sets of imaging data, the processor may be configured to direct one or more focusing devices that are operatively coupled to the imaging sensor and/or the imaging unit to adjust an alignment of the imaging sensor with respect to the imaging unit. Such calibration of the imaging sensor and/or the camera may improve alignment between an image generated using the first set of imaging data and another image generated using the second set of the imaging data. The calibration may be performed by the processor (e.g., upon user instruction or automatically) (i) prior to use of the imaging device for imaging the target site and/or (ii) in real time during the imaging of the target site.

In another aspect, the present disclosure provides a method of using the imaging systems described herein. The method may comprise providing an imaging module, where the imaging module comprises one or more of an imaging sensor, an imaging unit, one or more optical elements, and a processor. The method may further comprise using the imaging module to obtain one or more light signals. The method may further comprise using the one or more light signals to generate one or more images. The method may further comprise using the one or more images to render a dynamic visualization of the surgical scene.

In another aspect, the method may comprise (1) receiving a plurality of optical signals, (2) directing a first set of the optical signals to the imaging unit and directing a second set of the optical signals to the imaging sensor (e.g., infrared sensor), and (3) generating one or more images of the surgical scene using the first and second sets of light signals.

In another aspect, the present disclosure provides a method of imaging a target site, the method comprising receiving a first optical signal and a second optical signal from the target site where the first optical signal and the second optical signal each comprise a distinct wavelength range, directing the first optical signal to a first imaging unit, where the first imaging unit is integrated within a housing of a laparoscope or an endoscope, coupling a second imaging unit to the laparoscope or the endoscope, and directing the second optical signal to the second imaging unit.

In another aspect, the method may comprise adjusting a focus of the second optical signal on the second imaging unit. In an example, the method includes adjusting an orientation of the first imaging unit relative to the second imaging unit. In an example, the adjusting comprises rotating the first imaging unit relative to an insertion portion of the laparoscope or the endoscope.

Figure 4:
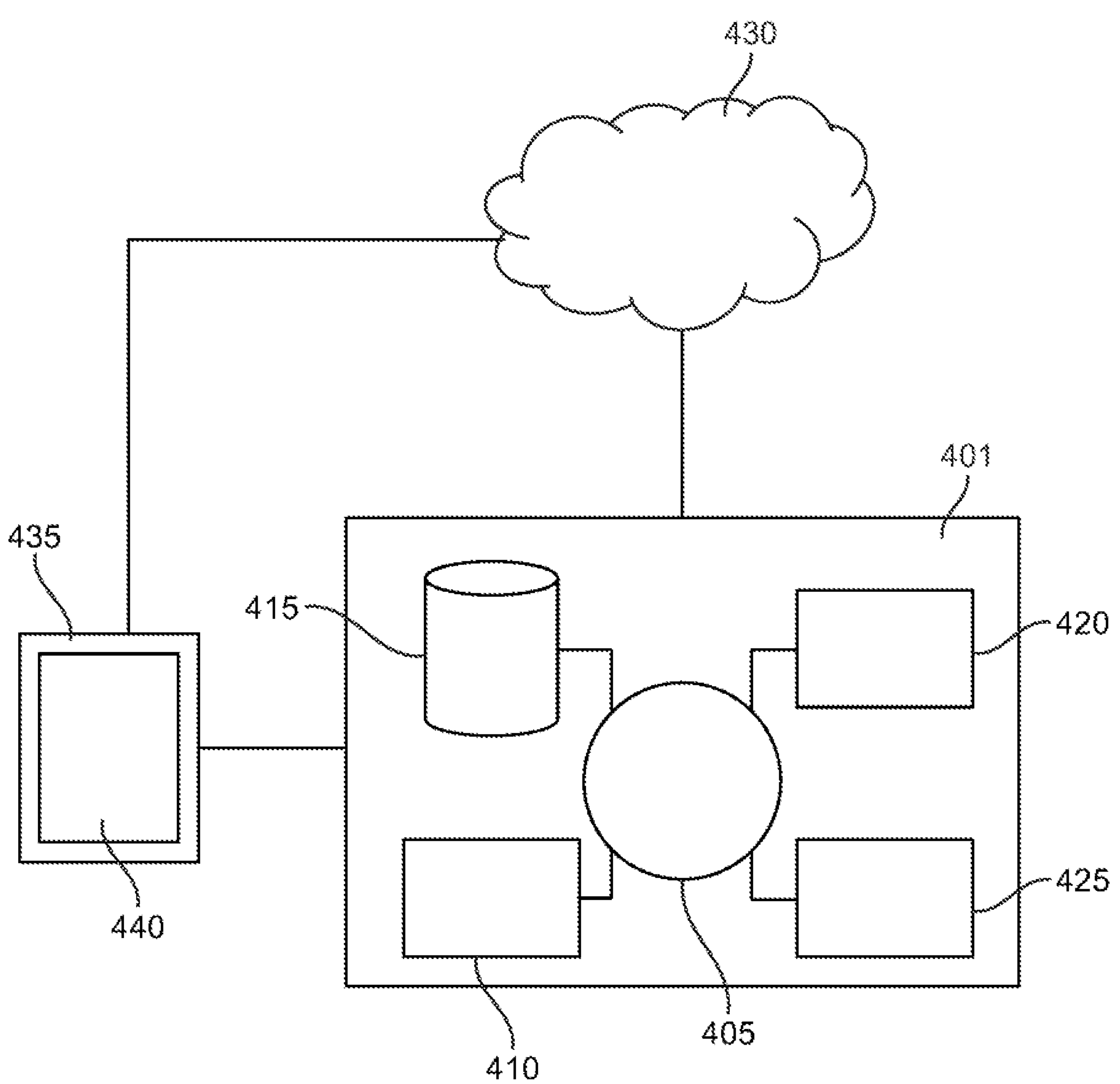
FIG. 4 schematically illustrates an example of a computer system that can be configured to implement the imaging methods of the present disclosure, in accordance with some embodiments.

In some cases, the present disclosure provides computer systems that are programmed or otherwise configured to implement methods of the disclosure, e.g., any of the subject methods for medical imaging. FIG. 4 shows a computer system 401 that is programmed or otherwise configured to implement a method for medical imaging. The computer system 401 may be configured to, for example, implement a method comprising generating one or more images of the surgical scene using a first set of optical signals (e.g., light signals) and a second set of optical signals. The first and second set of light signals may be transmitted from one or more optical elements of imaging devices and systems of the present disclosure, after reflecting off of, or being produced by, a target site within the field of view 106 of the distal end of the scope 105. The computer system 401 can be an electronic device of a user or a computer system that is remotely located with respect to the electronic device. The electronic device can be a mobile electronic device.

The computer system 401 may include a central processing unit (CPU, also "processor" and "computer processor" herein) 405, which can be a single core or multi core processor, or a plurality of processors for parallel processing. The computer system 401 also includes memory or memory location 410 (e.g., random-access memory, read-only memory, flash memory), electronic storage unit 415 (e.g., hard disk), communication interface 420 (e.g., network adapter) for communicating with one or more other systems, and peripheral devices 425, such as cache, other memory, data storage and/or electronic display adapters. The memory 410, storage unit 415, interface 420 and peripheral devices 425 are in communication with the CPU 405 through a communication bus (solid lines), such as a motherboard. The storage unit 415 can be a data storage unit (or data repository) for storing data. The computer system 401 can be operatively coupled to a computer network ("network") 430 with the aid of the communication interface 420. The network 430 can be the Internet, an internet and/or extranet, or an intranet and/or extranet that is in communication with the Internet. The network 430 in some cases is a telecommunication and/or data network. The network 430 can include one or more computer servers, which can enable distributed computing, such as cloud computing. The network 430, in some cases with the aid of the computer system 401, can implement a peer-to-peer network, which may enable devices coupled to the computer system 401 to behave as a client or a server.

The CPU 405 can execute a sequence of machine-readable instructions, which can be embodied in a program or software. The instructions may be stored in a memory location, such as the memory 410. The instructions can be directed to the CPU 405, which can subsequently program or otherwise configure the CPU 405 to implement methods of the present disclosure. Examples of operations performed by the CPU 405 can include fetch, decode, execute, and writeback.

The CPU 405 can be part of a circuit, such as an integrated circuit. One or more other components of the system 401 can be included in the circuit. In some cases, the circuit is an application specific integrated circuit (ASIC).

The storage unit 415 can store files, such as drivers, libraries and saved programs. The storage unit 415 can store user data, e.g., user preferences and user programs. The computer system 401 in some cases can include one or more additional data storage units that are located external to the computer system 401 (e.g., on a remote server that is in communication with the computer system 401 through an intranet or the Internet).

The computer system 401 can communicate with one or more remote computer systems through the network 430. For instance, the computer system 401 can communicate with a remote computer system of a user (e.g., a subject, an end user, a consumer, a healthcare provider, an imaging technician, etc.). Examples of remote computer systems include personal computers (e.g., portable PC), slate or tablet PC's (e.g., Apple® iPad, Samsung® Galaxy Tab), telephones, Smart phones (e.g., Apple® iPhone, Android-enabled device, Blackberry®), or personal digital assistants. The user can access the computer system 401 via the network 430.

Methods as described herein can be implemented by way of machine (e.g., computer processor) executable code stored on an electronic storage location of the computer system 401, such as, for example, on the memory 410 or electronic storage unit 415. The machine executable or machine readable code can be provided in the form of software. During use, the code can be executed by the processor 405. In some cases, the code can be retrieved from the storage unit 415 and stored on the memory 410 for ready access by the processor 405. In some situations, the electronic storage unit 415 can be precluded, and machine-executable instructions are stored on memory 410.

The code can be pre-compiled and configured for use with a machine having a processor adapted to execute the code, or can be compiled during runtime. The code can be supplied in a programming language that can be selected to enable the code to execute in a pre-compiled or as-compiled fashion.

Aspects of the systems and methods provided herein, such as the computer system 401, can be embodied in programming. Various aspects of the technology may be thought of as "products" or "articles of manufacture" typically in the form of machine (or processor) executable code and/or associated data that is carried on or embodied in a type of machine readable medium. Machine-executable code can be stored on an electronic storage unit, such as memory (e.g., read-only memory, random-access memory, flash memory) or a hard disk. "Storage" type media can include any or all of the tangible memory of the computers, processors or the like, or associated modules thereof, such as various semiconductor memories, tape drives, disk drives and the like, which may provide non-transitory storage at any time for the software programming. All or portions of the software may at times be communicated through the Internet or various other telecommunication networks. Such communications, for example, may enable loading of the software from one computer or processor into another, for example, from a management server or host computer into the computer platform of an application server. Thus, another type of media that may bear the software elements includes optical, electrical and electromagnetic waves, such as used across physical interfaces between local devices, through wired and optical landline networks and over various air-links. The physical elements that carry such waves, such as wired or wireless links, optical links or the like, also may be considered as media bearing the software. As used herein, unless restricted to non-transitory, tangible "storage" media, terms such as computer or machine "readable medium" refer to any medium that participates in providing instructions to a processor for execution.

Hence, a machine readable medium, such as computer-executable code, may take many forms, including but not limited to, a tangible storage medium, a carrier wave medium or physical transmission medium. Non-volatile storage media including, for example, optical or magnetic disks, or any storage devices in any computer(s) or the like, may be used to implement the databases, etc. shown in the drawings. Volatile storage media include dynamic memory, such as main memory of such a computer platform. Tangible transmission media include coaxial cables, copper wire and fiber optics, including the wires that comprise a bus within a computer system. Carrier-wave transmission media may take the form of electric or electromagnetic signals, or acoustic or light waves such as those generated during radio frequency (RF) and infrared (IR) data communications. Common forms of computer-readable media therefore include for example: a floppy disk, a flexible disk, hard disk, magnetic tape, any other magnetic medium, a CD-ROM, DVD or DVD-ROM, any other optical medium, punch cards paper tape, any other physical storage medium with patterns of holes, a RAM, a ROM, a PROM and EPROM, a FLASH-EPROM, any other memory chip or cartridge, a carrier wave transporting data or instructions, cables or links transporting such a carrier wave, or any other medium from which a computer may read programming code and/or data. Many of these forms of computer readable media may be involved in carrying one or more sequences of one or more instructions to a processor for execution.

The computer system 401 can include or be in communication with an electronic display 435 that comprises a user interface (UI) 440 for providing, for example, a portal for a healthcare provider or an imaging technician to view one or more medical images obtained using the imaging systems disclosed herein. The portal may be provided through an application programming interface (API). A user or entity can also interact with various elements in the portal via the UI. Examples of UI's include, without limitation, a graphical user interface (GUI) and web-based user interface.

Methods and systems of the present disclosure can be implemented by way of one or more algorithms. An algorithm can be implemented by way of software upon execution by the central processing unit 405. For example, the algorithm may be configured to generate one or more images of the surgical scene using a first set of optical signals (e.g., light signals) and a second set of optical signals. The first and second set of light signals may comprise light that is reflected from or produced by a target site or a target tissue within the field of view provided by the distal end of the scope.

The following references are incorporated herein by reference for all purposes, U.S. Pat. No. 9,271,633B2; U.S. Pat. No. 9,554,692B2; U.S. Pat. No. 9,155,480B2; US2014/0071257; U.S. Pat. No. 10,925,465; US2020/00107710; and U.S. Pat. No. 9,918,640.

While preferred embodiments of the present disclosure have been shown and described herein, it will be obvious to those skilled in the art that such embodiments are provided by way of example only. It is not intended that the disclosure be limited by the specific examples provided within the specification. While the disclosure has been described with reference to the aforementioned specification, the descriptions and illustrations of the embodiments herein are not meant to be construed in a limiting sense. Numerous variations, changes, and substitutions will now occur to those skilled in the art without departing from the disclosure. Furthermore, it shall be understood that all aspects of the disclosure are not limited to the specific depictions, configurations or relative proportions set forth herein which depend upon a variety of conditions and variables. It should be understood that various alternatives to the embodiments described herein may be employed in practicing the disclosure. It is therefore contemplated that the disclosure shall also cover any such alternatives, modifications, variations or equivalents. It is intended that the following claims define the scope of the disclosure and that methods and structures within the scope of these claims and their equivalents be covered thereby.

What is claimed is:

1. An imaging device comprising:

a housing;

an insertion portion of the housing, the insertion portion having an elongated optical axis, wherein a first optical signal and a second optical signal are transmitted along the elongated optical axis, wherein the first optical signal and the second optical signal each have a distinct wavelength range;

a beam splitter configured to deliver the first optical signal to a first imaging unit and configured to deliver the second optical signal to a second imaging unit;

one or more markers along the elongated optical axis; and a focusing lens on an optical path of either the first imaging unit or the second imaging unit, wherein adjustment of the focusing lens is configured to bring an image of the one or more markers into focus on both of the first imaging unit and the second imaging unit, and wherein a field of view of an image from the first imaging unit includes the image of the one or more markers configured to aid in one of positioning or alignment of the first imaging unit relative to the second imaging unit.

2. The imaging device of claim 1, wherein the first imaging unit comprises an infrared imaging sensor.

3. The imaging device of claim 1, wherein the first imaging unit, the second imaging unit, or both comprises a camera or a sensor for RGB imaging.

4. The imaging device of claim 1, wherein the distinct wavelength ranges of the first and second optical signals are separated by a threshold wavelength between about 700 nanometers (nm) to about 800 nm.

5. The imaging device of claim 1, wherein the first optical signal is a laser speckle imaging signal, and wherein the second optical signal is an RGB imaging signal.

6. The imaging device of claim 1, wherein the imaging units have different imaging modalities selected from a group consisting of an infrared imaging sensor for laser speckle imaging, a fluorescence imaging sensor for fluorescence imaging, a mosaic sensor for hyperspectral imaging, a short wave infrared (SWIR) sensor for SWIR imaging, and a depth sensor for depth imaging.

7. The imaging device of claim 1, further comprising a processor operatively coupled to either imaging unit or both and configured to process one or more images of a surgical scene to produce a visualization of the surgical scene.

8. The imaging device of claim 7, wherein the visualization of the surgical scene includes a dynamic overlay of images based on one or more imaging modalities selected from a group consisting of a laser speckle image, a depth image, a fluorescence image, and an RGB image of the surgical scene.

9. The imaging device of claim 1, wherein the image of the one or more markers comprises a notch or a fiducial marker.

10. The imaging device of claim 1, wherein the elongated optical path comprises one or more obstructions each between a pair of lenses, and wherein the one or more obstructions appear in the field of view as the image of the one or more markers.

11. The imaging device of claim 1, further comprising an optical source configured to project one or more visual references onto a surgical scene, and wherein the one or more visual references appear in the field of view as the image of the one or more markers.

12. The imaging device of claim 1, wherein the elongated optical path comprises one or more lenses for adjusting the field of view or an angle of view of a surgical scene.

13. The imaging device of claim 1, wherein the elongated optical path comprises one or more rod lenses or objective assemblies.

14. The imaging device of claim 1, wherein an elongated portion of the optical path includes one or more optical filters.

15. A system comprising:

a housing;

an insertion portion of the housing, the insertion portion having an elongated optical axis, wherein a first optical signal and a second optical signal are transmitted along the elongated optical axis, wherein the first optical signal and the second optical signal each have a distinct wavelength range;

a beam splitter configured to deliver the first optical signal to a first imaging unit and configured to deliver the second optical signal to a second imaging unit, wherein the second imaging unit is releasably attached to the system;

one or more markers along the elongated optical axis; and a focusing lens on an optical path of either the first imaging unit or the second imaging unit, wherein adjustment of the lens is configured to bring an image of the one or more markers into focus on both of the first imaging unit and the second imaging unit.

16. The system of claim 15, wherein the first imaging unit is rotatable relative to (i) the second imaging unit, (ii) an elongated portion of the housing, or (iii) both.

17. The system of claim 15, wherein the one or more markers includes first and second sets of fiducial marks, and wherein the first set of fiducial marks has finer or narrower notches as compared to the second set of fiducial marks.

18. The system of claim 17, wherein differences in resolution of the notches between the first set of fiducial marks and the second set of fiducial marks are used to determine an adjustment needed to focus.

19. A system comprising:

a housing;

an insertion portion of the housing, the insertion portion having an elongated optical axis, wherein a first optical signal and a second optical signal are transmitted along the elongated optical axis, wherein the first optical signal and the second optical signal each have a distinct wavelength range;

a beam splitter configured to deliver the first optical signal to a first imaging unit and configured to deliver the second optical signal to a second imaging unit, wherein the second imaging unit is releasably attached to the system;

first and second sets of fiducial marks along the elongated optical axis, wherein the first set of fiducial marks has finer or narrower notches as compared to the second set of fiducial marks, and wherein differences in resolution of the notches between the first set of fiducial marks and the second set of fiducial marks are used to determine an adjustment needed to focus;

a lens on an optical path of either the first imaging unit or the second imaging unit, wherein the optical path is rotatable relative to the first imaging unit, and wherein the lens is adjustable to bring an image of the first and second sets of fiducial marks into focus on both of the first imaging unit and the second imaging unit; and an image processor operatively coupled to the first imaging unit, the second imaging units or both and configured to determine the adjustment needed to focus based on the differences in resolution of the notches of the first and second sets of fiducial marks.

* * * * *